United States Patent [19]

Ishii et al.

[11] Patent Number: 5,024,844
[45] Date of Patent: Jun. 18, 1991

[54] PROCESS FOR THE PRODUCTION OF DRIED EARTHWORM POWDER AND ANTIHYPERLIPEMIC, ANTIDIABETIC, ANTIHYPERTENSIVE AND ANTIHYPOTENSIVE PREPARATIONS CONTAINING DRIED EARTHWORM POWDER AS ACTIVE INGREDIENT

[75] Inventors: Yoichi Ishii; Hisashi Mihara, both of Miyazaki, Japan

[73] Assignee: Eimei Company, Ltd., Miyazaki, Japan

[21] Appl. No.: 228,672

[22] Filed: Aug. 5, 1988

[30] Foreign Application Priority Data

Aug. 18, 1987 [JP] Japan ................. 62-204904
Aug. 18, 1987 [JP] Japan ................. 62-204905
Apr. 19, 1988 [JP] Japan ................. 63-094541
Apr. 19, 1988 [JP] Japan ................. 63-094542

[51] Int. Cl.$^5$ ............................. A61K 35/56
[52] U.S. Cl. ................. 424/520; 424/94.64; 514/2; 514/21; 514/866; 530/855
[58] Field of Search ............ 424/95, 94.64; 514/2, 514/21, 866; 530/855

[56] References Cited

U.S. PATENT DOCUMENTS 3,719,496  3/1973  Chen ............................ 424/95
4,350,625  9/1982  Abe ............................. 424/95
4,390,630  6/1983  Sawyer ......................... 424/95
4,568,545  2/1986  Mihara et al. ................. 514/882

FOREIGN PATENT DOCUMENTS 0126770   7/1983  Japan ........................... 424/95
59-16572  2/1984  Japan .
60-2965   4/1985  Japan .
1128149  12/1966  United Kingdom .
2116565   9/1983  United Kingdom .

OTHER PUBLICATIONS

Hisashi Mihara et al.; Acta Haematologica Japonica, vol. 45, p. 503 (1982).
Hisashi Mihara; Reports of Special Research Project on Environmental Science, B 304-R 30, vol. 4, p. 108 (1986) (copy and translated abstract).

Primary Examiner—Douglas W. Robinson
Assistant Examiner—Jean C. Witz
Attorney, Agent, or Firm—Oblon, Spivak, McClelland, Maier & Neustadt, P.C.

[57] ABSTRACT

Disclosed is a process for the production of dried earthworm powder which comprises the steps of leaving a species of living earthworms in fresh water or a slightly acidic aqueous solution until the alimentary canal thereof is freed of soil, wet-grinding the living earthworms, and freeze-drying and then vacuum-drying the resulting suspension under a vacuum of 10 mmHg or below for 10 to 100 hours while raising the temperature stepwise from $-60°$ C. to 80° C. This dried earthworm powder may be combined with pharmaceutically acceptable carriers to form pharmaceutical compositions which are useful for the treatment or prevention of hyperlipemia, diabetes, hypertension and hypotension in human beings.

4 Claims, No Drawings

PROCESS FOR THE PRODUCTION OF DRIED EARTHWORM POWDER AND ANTIHYPERLIPEMIC, ANTIDIABETIC, ANTIHYPERTENSIVE AND ANTIHYPOTENSIVE PREPARATIONS CONTAINING DRIED EARTHWORM POWDER AS ACTIVE INGREDIENT

BACKGROUND OF THE INVENTION (1) Field of the Invention

This invention relates to a process for the production of dried earthworm powder, as well as antihyperlipemic, antidiabetic and blood pressure regulator (antihypertensive and/or antihypotensive) preparations containing the dried earthworm powder as the active ingredient. More particularly, it relates to a novel and improved process for the production of pharmaceutically acceptable dried earthworm powder which has not only excellent antihyperlipemic, antidiabetic (or hypoglycemic), antihypertensive and/or antihypotensive effects but also a high degree of safety, as well as antihyperlipemic, antidiabetic and blood pressure regulator (antihypertensive and/or antihypotensive) preparations containing the dried earthworm powder as the active ingredient. Thus, the dried earthworm powder produced by the process of the present invention may be combined with pharmaceutically acceptable carriers to form pharmaceutical compositions which are useful for the treatment or prevention of hyperlipemia, diabetes, hypertension and hypotension in mammals and, in particular, human beings.

(2) Description of the Prior Art

It is recognized that hyperlipemia, along with hypertension, diabetes and smoking, is an important causative factor in arteriosclerosis, and a variety of antihyperlipemic drugs comprising synthetic organic compounds have been developed and used for the treatment and prevention of hyperlipemia. Typical examples thereof are clofibrate and nicomol. However, it is known that clofibrate and its derivatives may frequently cause muscle pain, hepatic functional disorders and gallstones formation. It is also known that nicomol has side effects such as facial suffusion and gastrointestinal disorders. Moreover, it has been reported that clofibrate may produce hepatoma in animals [D. J. Svoboda et al., Cancer Res., Vol. 39, p. 3419 (1979)].

In addition to the above-described problem of safety, special attention is also paid to the effect and pharmacology of antihyperlipemic drugs. Specifically, with the recent progress of research on the metabolism of lipids and, in particular, the functions of serum lipoproteins as serum lipid carriers, much importance has come to be attached not only to the ability of a drug to reduce the concentration of lipids in the serum, but also to its action on lipoproteins.

Serum cholesterol, together with triglycerides (hereinafter referred to as TG), phospholipids (hereinafter referred to as PL) and apoproteins, forms lipoproteins. According to density, these lipoproteins are divided into very low density lipoprotein (hereinafter referred to as VLDL), low density lipoprotein (hereinafter referred to as LDL) and high density lipoprotein (hereinafter referred to as HDL). Among these lipoproteins, VLDL and LDL are thought to induce arteriosclerosis. In contrast, HDL functions to participate in the transport of cholesterol from peripheral blood vessels to the liver, the formation of cholesterol ester and the catabolism of TG, and is believed to have the effect of preventing and retracting arteriosclerosis.

Accordingly, in the future development of an antihyperlipemic drug, importance should be attached not only to its effect of reducing the level of total cholesterol (hereinafter referred to as TC) in the serum, but also to the type of lipoprotein whose cholesterol it can act. In particular, it would be desirable to develop a drug not only having the effect of reducing the level of cholesterol in LDL (hereinafter referred to as LDL-C) and elevating the level of cholesterol in HDL (hereinafter referred to as HDL-C), but also having the effect of lowering the arteriosclerosis index (hereinafter referred to as AI) which is calculated from the formula: (TC - HDL-C)/HDL-C.

Conventionally, organic synthetic compounds such as sulfonylurea compounds and biguanide compounds have been widely used as oral antidiabetic drugs. Generally, antidiabetic drugs are medicines used to normalize the metabolism in the morbid state, and not medicines capable of curing diabetes itself. In the case of diabetic coma or juvenile diabetes, oral antidaibetic drugs are ineffective and insulin alone is effective. In several forms of diabetes in which insulin is mandatory (for example, diabetes associated with ketoacidosis or serious infection), oral antidiabetic drugs are ineffective. The chief indication for the use of oral antidiabetic drugs is maturity-onset diabetes which cannot be fully controlled by alimentotherapy. Also in this case, such oral antidiabetic drugs tend to produce side effects such as hypoglycemia, hepatic functional disorders and anorexia, and must be used under the rigid control of a physician. Thus, there is an eager demand for an antidiabetic drug having no side effects.

In recent years, there are a large numbers of patients with hypertension or hypotension, irrespective of age. In order to treat such patients, hypotensors are often administered to hypertensive patients and, though not mandatory, hypertensors (or pressors) are often administered to hypotensive patients.

Especially with the recent increase in the number of hypertensive patients, a wide variety of remedies for hypertension (or hypotensors) have been being developed and used. Once hypertensive patients begin to take a hypotensor, discontinuance of its use may cause the symptoms to become worse than before. Accordingly, it is often necessary to take the drug continuously for a long period of time. Also in the case of hypotensive patients to whom a drug is administered, its administration is often continued for a long period of time. Thus, there is an eager demand for a drug having no side effects.

For example, hydralazine known to be a hypotensor has the effect of dilating peripheral blood vessels and exhibits excellent hypotensive activity. However, it may cause tachycardia as a side effect, so that it is used in combination with a β-blocker. Generally, hypotensors and hypertensors are used for a long of time, so that it would be highly desirable to provide such drugs having no side effects.

Especially in the Oriental countries, earthworms (also called "dilong") have been used as a drug from remote antiquity. The following pharmacological effects of easthworms have been reported in the literture.

(1) Shinryu Ofuchi ["Mimizu-to-Jinsei (Earthworms and Human Life)", Maki Shobo, Oct. 30, 1947, pp. 223-226] and Nikiji Hatai ["Mimizu (Earthworms), Reprinted Edition", Scientist Co., Apr. 30, 1980, pp. 160-163] have reported that earthworms have a variety of pharmacological activities, i.e., they are effective in reducing the size of vesical calculi and eliminating them from the body, in the treatment of jaundice, and as a parturifacient, restrative, hair grower, tonic and an antipyretic. On the other hand, they have also reported some toxic actions of earthworms. That is, earthworm poison injures the nervous systems and causes hemolysis (or the destruction of red blood cells).

(2) The following description is found in "Pharmaceutical Dictionary of the People's Republic of China" edited by the Pharmaceutical Dictionary Editing Committee, the Department of Hygienics, the People's Republic of China (1977 Edition, Part I, pp. 197-198).

Conventionally, there are two types of dilong. One of them is wide dilong (*Lumbricus kwangtungesis*) that is produced by cutting the body of each earthworm open, washing off the guts and soil, and drying it in the sun, in the shade or at low temperature. The other is soil dilong (*Lumbricus nativus*) that is produced by by killing earthworms in ash from plants, freeing them of ash, and drying them in the sun, in the shade or at low temperature. The dried earthworm so produced have soil within the body thereof. It is reported therein that these two types of dilong are used in a daily dose of 4.5 to 9 g as an antipyretic, anticonvulsant, circulation promoter, remedy for hemiplegia, articular analgesic, diuretic, antiasthmatic and antihypertensive.

(3) It is described in "Our Chinese Medicine Series 3: Dilong and Cuttlebone—Scientific Research in China" (Matsuura Yakugyo K. K., p. 7) that dilong tincture (i.e., an ethyl alcohol extract of dilong) has an hypotensive effect.

(4) It has been reported by Takuo Okuda ("Encyclopedia of Natural Medicines", Hirokawa Shoten, Apr. 15, 1986, p. 215) that dilong is being used as an antipyretic, analgesic, diuretic and antidote.

(5) Mamotu Tanaka [Hokkaido Medical Journal, Vol. 24, pp. 18-24 (1949)] has reported the results of an experiment with earthworms. Specifically, small pieces of dried earthworms were freed of soil and then extracted with boiling water. After the resulting extract was concentrated, ethyl alcohol was added thereto and the precipitated material (lumbrofebrin) was dissolved in Ringer's solution. When this solution was intravenously injected into an anesthetized cat, a sudden fall in blood pressure was caused. In addition, acceleration of blood coagulation was observed in proportion to the shock.

(6) Kenjiro Ikawa [Yamaguchi Igaku, Vol. 9, pp. 571-576 (1960)] has reported that test solutions were prepared by extracting dilong with physiological saline, or by extracting dilong with ethyl alcohol or acetone, evaporating the extract to dryness and dissolving the residue in physiological saline. When each of these test solutions was intravenously injected into a mature rabbit, a fall in blood pressure was observed.

(7) It is reported in "Enzyclopedia of Chinese Medicines, Volume Two" edited by the Koso New Medical Institute (Shanghai Scientific and Technical Publishing Company, 1980, p. 2112) that, when wide dilong tincture, a suspension of dried earthworm powder, a hot water infusion of earthworms, or a decoction of earthworms was administered to anesthetized dogs, big rats, cats, or mice with chronic renal hypertension, a slow and long-lasting hypetnesive effect was noted. When dilong extract was intravenously injected into anethetized dogs or cats, a rapid hypotensive effect appeared. However, it is also reported that they were ineffective when administered orally and when used in clinical trials. Moreover, it is reported in the same book (p. 2114) that essential hypertension could be effectively controlled by oral administration of dilong. To this end, 10 ml of 40% dilong tincture (prepared by steeping 40 g of dilong in 100 ml of 60% ethyl alcohol) was given three times a day [i.e., in a daily dose of 12 g of dilong (as calculated by the present inventors)] and this treatment was continued for 30 to 60 days. For those who could not drink the tincture, pills were prepared from pure dilong powder mixed with water (and a small amount of filler, and 3 to 4 g of the pills were given three times a day [in a daily dose of 9 to 12 g of dilong (as calculated by the present inventors)]. Furthermore, it is reported that essential hypertension could also be effectively controlled by administering 2 ml of dilong $B_1$ liquid (prepared by removing hypoxanthine from dilong with the aid of $HgCl_2$ and then isolating hypotensive components therefrom by means of an ion-exchange resin) three times a day [in a daily dose of 24 g of dilong (as calculated by the present inventors)].

Conventional methods for producing the dried products of dried powder of earthworms are roughly divided into the following three types.

(i) The method in which the body of each earthworm is cut open, freed of its contents (i.e., the guts and soil), and then dried in the sun, in the shade or at low temperature (usually 50° C. or below).

(ii) The method in which earthworms are killed by placing them in ash from plants or charcoal, freed of any soil, and then dried in the sun, in the shade or at low temperature (usually 50° C. or below) to obtain dried earthworms having soil therein.

(iii) The method in which earthworms are freed of the soil present in their body and then dried by placing them in ash from plants or charcoal.

In case of need, the dried earthworms thus obtained are reduced to powder and used. The above-described methods are simple and economical ones and has the advatage that they can easily be carried out at home. However, if the dried earthworms (or dried earthworm powder) produced by these methods are preserved in an open state either in a referigerator at 0° to 5° C. or in a room at 5° to 45° C., they will become moldy within about 6 months and cannot be used any longer. Even if they are preserved in a well-closed state, they will become moldy within a year.

Where dried earthworms having soil within the body thereof, as produced by the aforesaid method (ii), or earthworms dried in ash from plants or charcoal, as produced by the aforesaid method (iii), are used as a medicine, it is common practice to extract them with hot water or decoct them in boiling water, filter the resulting extract or decoction, and take the filtrate. In particular, it is seldom that the dried earthworms produced by method (ii) is used in the form of dilong tincture, powder or pills.

The dried earthworms produced by method (i) are frequently used as a hot water infusion or decoction, or in the form of dilong tincture, dilong powder or pills (prepared from dilong powder mixed with a small amount of water or a small amount of filler). In the case of methods (ii) and (iii), the yield of dried earthworms having a moisture content of 10 to 16% is 5 to 19% based on the living earthworms used as the raw material.

Recently, Yoichi Ishii who is one of the present inventors has proposed a health food comprising, as principal components, the proteins and lipids derived from earthworms, and a process for producing the same [Japanese Patent Laid-Open No. 216572/'84 (date of laying open: Dec. 6, 1984)]. This process is an excellent one for the purpose of producing dried earthworm powder as a health food. However, as a method for producing dried earthworm powder for use as antihyperlipemic, abtidiabetic and blood pressure regulating drugs, the aforesaid process is not satisfactory from the viewpoint of efficacy. Specifically, if an external action is exerted on living earthworms to eliminate the soil present in the body thereof, it is impossible to remove the soil selectively. It has been found that, even if the utmost care is taken, the internal organs and body fluids containing the major portion of components highly important from the viewpoint of medicinal effects is at least partially removed together with the soil, resulting in insufficient efficacy. Moreover, the yield is as low as 10 to 19% based on the living earthworms used as the raw material. Furthermore, it is a great disadvantage that, since the final stage of vacuum drying is carried out at 80° C. under a vacuum of 0.3 torr for a long period of 20 hours or more, the enzymes present in the dried earthworm powder and playing an important role in the manifestation of medicinal effects are at least partially destroyed or inactivated. Accordingly, the antihypertensive effect of the dried earthworm powder produced by the process of Japanese Patent Laid-Open No. 216572/'84 has been found to be about 50% of that of the dried earthworm powder produced by the process of the present invention.

Recently, Hisahi Mihara, who is one of the present inventors, and his collaborators have demonstrated that the fibrinolytic substance derived from earthworms is an enzyme protein which has an optimum pH of 8 to 10; is stable in the pH range of 5 to 10; is inhibited by Trazirol (trade name), Transamine (trade name), soybean trypsin inhibitor and serum; has plasminogen-activating and fibrynolytic effects; and has no fibrinogenolytic effect.

A crude enzyme protein fraction obtained by extraction of an earthworm with an aqueous medium, and a process for the preparation of a fibrinolytic substance by purifying the crude enzyme enzyme protein fraction are disclosed in Japanese Patent Laid-Open No. 148824/'83 (filed Feb. 27, 1982) and its corresponding foreign patent applications including U.S. patent application Ser. No. 470,394 (filed Feb. 28, 1983), U.K. Pat. Appln. No. 8305359 (filed Feb. 25, 1983), Italian pat. appln. No. 477954A (filed Feb. 25, 1983), French Pat. Appln. No. 03165 (filed Feb. 25, 1983), German Pat. Appln. No. P3306944.1 (filed Feb. 28, 1983) and Canadian Pat. Appln. No. 422034 (filed Feb. 21, 1983).

Furthermore, Hisashi Mihara and his collaborators have derived six novel proteases from earthworms, as disclosed in Japanese Patent Laid-Open No. 63184/'84 (filed Oct. 2, 1982), and have developed a thrombolytic preparation comprising these proteases as the active ingredients, as disclosed in Japanese Patent Laid-Open No. 184131/'84 (filed Mar. 31, 1983). These inventions are also disclosed in their consolidated forein patent applications including Korean Pat. Appln. No. 2990 (filed Jul. 30, 1983), Au. Pat. Appln. No. 16293 (filed Jun. 27, 1983), Ca. Pat. Appln. No. 431387 (filed Jun. 28, 1983), Dk. Pat. Appln. No. 3008 (filed Jun. 29, 1983), Ep. Pat. Appln. No. 83106288.0 (filed Jun. 28, 1983), Es. Pat. Appln. No. 523754 (filed Jun. 30, 1983), Fi. Pat. Appln. No. 832383 (filed Jun. 29, 1983), No. Pat. Appln. No. 2399 (filed Jun. 30, 1983), Ph. Pat. Appln. No. 29151 (filed Jun. 30, 1983), Tw. Pat. Appln. No. 7211983 (filed Jun. 18, 1983) and U.S. patent application Ser. No. 508,163 (filed Jun. 27, 1983).

The present inventors made an investigation of the literature and obtained the following results:

(1) In the literature, no mention can be found of the antihyperlipemic effect of pharmaceutical preparations containing dried earthworm powder or dilong as the active ingredient. Still less, it is not reported therein that dried earthworm powder has not only the effect of reducing the serum TC level, but also the effect of reducing the serum LDL-C level and elevating the serum HDL-C level to cause a lowering of AI, and that dried earthworm powder is a highly safe drug which does not producing side effects such as hepatic hypertrophy and hepatic functional disorders.

(2) In the literature, no mention can be found of the antidiabetic or hypoglycemic effect of pharmaceutical preparations containing dried earthworm powder as the active ingredient.

That is, it is not reported in the literature that, in rats with diabetes experimentally induced by alloxan, the blood sugar level can be significantly reduced by administering dried earthworm powder thereto. As will be described later, capsules containing dried earthworm powder, in combination with alimentotherapy, were administered to diabetic patients for 4 to 9 months. Thus, in the case of patients with a mild or moderate degree of diabetes, the blood sugar level began to lower after 2 or 3 months of treatment, and returned to the normal value of healthy persons after 4 months of treatment. Such as excellent effect cannot be found in the literature.

(3) In the literature, no mention can be found of the antihypotensive effect of pharmaceutical preparations containing dried earthworm powder as the active ingredient. Moreover, it is not reported therein that dried earthworm powder has a blood pressure regulating effect, i.e., the administration of dried earthworm powder to patients with hypertension and/or hypotension restores their maximum and minimum blood pressures to normal.

SUMMARY OF THE INVENTION

It is an object of the present invention to provide a process for the production of dried earthworm powder by which a pharmaceutically acceptable and highly safe dried earthworm powder exhibiting excellent antihyperlipemic, antidiabetic or hypoglycemic, antihypertensive and/or antihypotensive activities without producing any side effects can be obtained in high yield.

It is another object of the present invention to provide antihyperlipemic, antidiabetic and blood pressure regulator (antihypertensive and/or hypotensive) preparations containing, as the active ingredient, the dried earthworm powder produced by the aforesaid process.

It is still another object of the present invention to provide a method for the treatment of hyperlipemia, diabetes, hypertension or hypotension in mammals and, in particular, human beings which comprises administering thereto such a preparation so as to counteract the disease without producing any side effects.

Other objects of the present invention will become apparent from the following detailed description.

Since antihyperlipemic drugs, antidiabetic or hypoglycemic drugs, and blood pressure regulating drugs (or antihypertensive or antihypotensive drugs) may involve prolonged use, they must not only have excellent efficacy, but also be safely usable without producing any side effects. As a means for achieving this purpose, the present inventors have carried on an intensive study for many years with a view to producing such highly safe and side-effect-free drugs from natural materials, particularly earthworms.

Specifically, it has been a first aim to develop a highly safe antihyperlipemic drug which has excellent antihyperlipemic activity, has the effect of reducing serum LDL-C and elevating serum HDL-C so as to lower the AI value, and does not produce side effects such as hepatic hypertrophy and hepatic functional disorders.

It has been a second aim to develop an antidiabetic drug which, when administered to maturity-onset diabetic patients in whom the diabetes cannot be fully controlled by alimentotherapy alone, is effective in the treatment and prevention of diabetes without producing side effects such as hypoglycemia, hepatic functional disorders and anorexia.

Hypotensors and hypertensors are thought to be drugs which act in entirely different ways. That is, hypotensors have the effect of reducing blood pressure and hypertensors have the effect of raising blood pressure, so that they must always be used under the supervision of a medical specialist. For example, when a definite hypotensive effect is produced by the use of a hypotensor, a suitable measure (such as a change of drug or a temporary cessation of the treatment) is taken according to the degree of hypertension. If an elevation in blood pressure has occurred, administration of the proper drug must be resumed. It would be desirable to treat hypertensive and/or hypotensive patients with a single drug. To this end, it is necessary to have a drug capable of restoring the maximum and minimum blood pressures of hypertensive and/or hypotensive patients to their normal levels. Moreover, since such an antihypertensive and/or antihypotensive drug involves prolonged use, a safe drug which will not produce any side effects is strongly desired. Thus, it has been a third aim to produce a highly safe and side-effect-free antihypertensive and/or antihypotensive drug from natural materials.

As described in the above-cited literature, it is known that dried earthworm products have a hypotensive effect. However, the yield of dried earthworm products obtained according to conventional techniques is as low as 5 to 19% based on the living earthworms used as the raw material. Moreover, even if such dried earthworm products are preserved in a well-closed container at room temperature (5° to 45° C.), they will become moldy or deteriorate within a year and become no longer suitable for medical use. Furthermore, such dried earthworm products have the disadvantage of being insufficient or inadequate in efficacy because of the partial destruction or inactivation of the enzymes present therein, and/or the disadvantage of producing side effects. Accordingly, the present inventors have made an effort to develop a process for producing dried earthworm powder in high yield without destroying or inactivating the enzymes present therein, so as to obtain sterile dried earthworm powder which has a high degree of safety without producing side effects such as hemolysis (i.e., destruction of red blood cells) and tachycardia, and can be preserved or stored in a well-closed state for at least 4 years.

DETAILED DESCRIPTION OF THE INVENTION

In order to solve the above-described problems, the present inventors have made an intensive study and have established a novel and improved processes for the production of dried earthworm powder. The process of the present invention will be fully described hereinbelow in accordance with two preferred embodiments.

PRODUCTION PROCESS 1

A species of living earthworms are placed in fresh water or an aqueous solution containing not greater than 0.3% by weight, preferably not greater than 0.1% by weight, of at least one compound selected from organic acids such as acetic acid, citric acid, succinic acid, malic acid, tartaric acid and lactic acid; inorganic acids such as phosphoric acid, sulfuric acid and hydrochloric acid; and sodium or potassium salts of these acids. The aforesaid solution can also be characterized as a slightly acidic aqueous solution having a pH of 3 to 6.5. These living earthworms are left therein at a temperature of 1° to 25° C., preferably 2° to 15° C., for a period of 0.5 to 72 hours, preferably 1 to 40 hours. Thus, the alimentary canal of the living earthworms is substantially freed of soil by their own excetory power. Then, the living earthworms are washed with water to remove any dirt from the body surfaces thereof.

Thereafter, the living earthworms are wet-ground and the resulting suspension is frozen at a low temperature of −5° C. or below, preferably −10° to −60° C. Then, the frozen suspension is freeze-dried and vacuum-dried. Specifically, while the temperature is raised stepwise from −60° to +90° C., preferably from −40° to +80° C., the suspension is freeze-dried and then vacuum-dried under a vacuum of 100 mmHg or below, preferably 30 mmHg or below, for a period of 5 to 100 hours, preferably 10 to 60 hours. Thus, there is obtained sterile dried earthworm powder.

PRODUCTION PROCESS 2

A species of living earthworms are washed with water to remove any dirt from the body surfaces thereof. Then, the living earthworms placed in fresh water or an aqueous solution containing not greater than 0.3% by weight, preferably not greater than 0.1% by weight, of at least one compound selected from organic acids such as acetic acid, citric acid, succinic acid, malic acid, tartaric acid and lactic acid; inorganic acids such as phosphoric acid, sulfuric acid and hydrochloric acid; and sodium or potassium salts of these acids. The aforesaid solution can also be characterized as a slightly acidic aqueous solution having a pH of 3 to 6.5. These living earthworms are left therein at a temperature of 1° to 25° C., preferably 2° to 15° C., for a period of 0.5 to 72 hours, preferably 1 to 40 hours. Thus, the alimentary canal of the living earthworms is substantially freed of soil by their own excetory power. Thereafter, the living earthworms are wet-ground and the resulting suspension is frozen at a low temperature of −5° C. or below, preferably −10° to −60° C. Then, the frozen suspension is freeze-dried and vacuum-dried. Specifically, while the temperature is raised stepwise from −60° to +90° C., preferably from −40° to +80° C., the suspension is freeze-dried and then vacuum-dried under a vacuum of 100 mmHg or below, preferably 30 mmHg or below, for a period of 5 to 100 hours, preferably 10 to 60 hours. Thus, there is obtained sterile dried earthworm powder.

In the step of wet-grinding the earthworms, i.e., the step of destroying the tissues (or cells) of the earthworms, it is preferable to form the earthworms into a suspension or homogenate by means of a suitable device such as homogenizer, blender, homomixer, smasher or pressurized cell destroyer, This well-grinding step is desirably carried out at a temperature of 1° to 25° C. and preferably 2° to 15° C.

According to either of the above-described processes, dried earthworm powder having a yellowish-brown or brown color can be obtained from living earthworms in a 20 to 35% yield. In ordinary cases, the dried earthworm powder was prepared so as to have a moisture content of 5 to 16%, preferably 7 to 14%, an ash content of 3 to 8%, preferably 4 to 7%, and a nitrogen content of 1 to 11%, preferably 6 to 11%. The dried earthworm powder thus obtained contains about 18 amino acids including aspartic acid, threonine, serine, glutamic acid, proline, glycine, alanine, cysteine, valine, methionine, isoleucine, leucine, tyrosine, phenylalanine, tryptophan, lysine, histidine and arginine.

TEST 1

The results of rough analysis of several dried earthworm powder products obtained by the above-described Production Processes 1 and 2 are shown in Table 1.

TABLE 1

| Dried earthworm powder product | | Rough analysis | | |
|---|---|---|---|---|
| Process | Designation | Moisture (%) | Ash (%) | Nitrogen (%) |
| 1 | M-1 | 10.2 | 5.1 | 9.4 |
| 1 | M-2 | 10.4 | 5.3 | 8.6 |
| 1 | M-3 | 10.7 | 5.2 | 9.2 |
| 1 | M-4 | 10.6 | 5.6 | 9.6 |
| 2 | M-5 | 9.5 | 4.5 | 7.8 |
| 2 | M-6 | 9.2 | 4.7 | 8.4 |
| 2 | M-7 | 9.7 | 4.6 | 8.2 |
| 2 | M-8 | 10.1 | 5.5 | 9.7 |
| 2 | M-9 | 10.2 | 5.6 | 9.9 |

TEST 2

The compositions of two dried earthworm powder products (M-2 and M-4) obtained by Production Process 1 and one dried earthworm powder product (M-5) obtained by Production Process 2 were analyzed. The results thus obtained are shown in Table 2.

TABLE 2

| | M-2 | M-4 | M-5 |
|---|---|---|---|
| Moisture | 10.4% | 10.6% | 9.5% |
| Crude proteins | 53.8% | 60.0% | 48.8% |
| Crude lipids | 12.2% | 9.4% | 14.2% |
| Soluble nitrogen free matter | 18.2% | 14.4% | 22.9% |
| Ash | 5.3% | 5.6% | 4.5% |
| Crude fibers | 0.1% | 0.1% | 0.1% |
| | (on a dry basis) | (on a dry basis) | (on a dry basis) |
| Ca | 0.384 g % | 0.389 g % | 0.318 g % |
| Mg | 0.194 g % | 0.202 g % | 0.166 g % |
| K | 0.613 g % | 0.624 g % | 0.508 g % |
| Na | 0.382 g % | 0.388 g % | 0.307 g % |
| P | 0.504 g % | 0.512 g % | 0.417 g % |
| Fe | 0.061 g % | 0.064 g % | 0.055 g % |
| Cu | 1.72 mg % | 1.78 mg % | 1.40 mg % |

TABLE 2-continued

| | M-2 | M-4 | M-5 |
|---|---|---|---|
| Zn | 5.63 mg % | 5.78 mg % | 4.84 mg % |
| Mn | 1.54 mg % | 1.66 mg % | 1.39 mg % |

TEST 3

Crude proteins were isolated from two dried earthworm powder products (M-2 and M-4) obtained by Production Process 1 and one dried earthworm powder product (M-5) obtained by Production Process 2, and then subjected to amino acid analysis. For purposes of comparison, two protein-rich foods (i.e., fish meal and soybean powder) were analyzed in the same manner. The results thus obtained are shown in Table 3.

TABLE 3

| | Dried earthworm powder products | | | Fish meal* | Soybean powder* |
|---|---|---|---|---|---|
| | M-2 | M-4 | M-5 | | |
| | (g/100 g) | | | (g/100 g) | (g/100 g) |
| Aspartic acid | 6.68 | 7.52 | 6.06 | — | — |
| Threonine | 2.97 | 3.34 | 2.68 | 2.56 | 1.95 |
| Serine | 3.06 | 3.42 | 2.77 | — | — |
| Glutamic acid | 8.27 | 9.31 | 7.67 | — | — |
| Proline | 1.23 | 1.37 | 1.09 | — | — |
| Glycine | 3.26 | 3.66 | 2.94 | 6.31 | 2.92 |
| Alanine | 3.69 | 4.14 | 3.41 | — | — |
| Cysteine | 0.59 | 0.65 | 0.55 | 0.59 | 0.90 |
| Valine | 3.26 | 3.63 | 2.99 | 2.83 | 2.44 |
| Methionine | 1.03 | 1.12 | 0.95 | 1.84 | 0.72 |
| Isoleucine | 3.02 | 3.38 | 2.83 | 2.43 | 2.25 |
| Leucine | 4.89 | 5.49 | 4.49 | 4.27 | 3.42 |
| Tyrosine | 2.47 | 2.77 | 2.21 | 1.91 | 1.71 |
| Phenylalanine | 2.73 | 3.02 | 2.55 | 2.37 | 2.14 |
| Tryptophan | 0.32 | 0.38 | 0.29 | — | — |
| Lysine | 4.47 | 5.28 | 4.49 | 1.25 | 1.06 |
| Histidine | 1.65 | 1.83 | 1.55 | 4.53 | 3.07 |
| Arginine | 4.18 | 4.47 | 3.81 | 4.20 | 3.53 |

*Based on the data given in P. McDonald, R. A. Edwards and J. F. D. Greenhalgh: Animal Nutrition (1973).

As can be seen from Tables 2 and 3, the dried earthworm powder products obtained by Production Processes 1 and 2 were rich in crude proteins, crude lipids and various metals, and the amino acid analysis of the crude proteins revealed that they contained high proportions of essential amino acids.

The dried earthworm powder products obtained by Production Process 1 was somewhat better than those obtained by Production Process 2. Moreover, when the living earthworms are left in an aqueous solution containing the aforesaid low concentration of at least one compound selected from an organic acid, an inorganic acid, and a sodium or potassium salt of such an acid, the alimentary canal thereof is evacuated more rapidly and more completely than when they are left in fresh water.

Hisashi Mihara and his collaborators have obtained six novel protease (or fibrinolytic enzyme) fractions from earthworms (Japanese Patent Laid-Open Nos. 63184/'84 and 184131/'84). Specifically, dried earthworm powder was mixed with 10 volumes of physiological saline and the resulting suspension was incubated for 2 days. The supernatant was fractionated with ammonium sulfate and the resulting precipitate was subjected to gel filtration using Sephacryl S-200. By subjecting the resulting protein fraction to DEAE-cellulose ion exchange chromatography, protein fractions I, II and III having caseinolytic and fibrinolytic activities were obtained. When these protein fractions I, II and III were further purified by means of DEAE-cellulose, Sephadex G-75, Toyopearl HW55, ACH-Sepharose, Benzamidine-Sepharose and the like, there were obtained six purified enzyme fractions. When molecular weight measurements were made with SDS-PAGE, fraction I-0 had the lowest molecular weight of 23,500. The molecular weights of fractions I-1, I-2, II, III-1 and III-2 increased in that order, that of fraction III-2 being 34,200. When the isoelectric points of these six fractions were measured by isoelectric-point electrophoresis, fraction I-0 had the highest electric point of pH 4.12. The isoelectric points of fractions I-1, I-2, II, III-1 and III-2 became lower in that order, that of fraction III-2 being pH 3.52. These six fractions are new peoteolytic enzymes different from serine enzymes. It has also been reported that these proteolytic enzymes have an optimum pH of around 8 or 8-10, are stable in the pH range of 4-12 or 5-12, have an optimum temperature of 50° C. or 50°-60° C., and are inactivated by heating at 70° C. for 60 minutes.

The fibrinolytic activity of the dried earthworm powder of the present invention was tested using the dried earthworm powder products M-4 and M-5 obtained by the above-described Production Processes 1 and 2. Specifically, one part of the dried earthworm powder product M-4 was mixed with 10 parts of physiological saline and the resulting supernatant was tested with a standard fibrin plate. As shown in Table 4, a fibrinolytic activity was observed at once. When the suspension of the dried earthworm powder product M-4 in physiological saline was incubated at 37° C., the fibrinolytic activity of its supernatant was increased about 4-fold on the 10th day, 5-fold on the 50th day, and 5.5-fold on the 75th day. This seems to suggest that large amounts of preoteolytic enzyme precursors are present in the dried earthworm powder and their enzyme activity is manifested as a result of autodigestion. When the activity of the supernatant is expressed in international units of urokinase, the activity observed on the 50th day was calculated to be about 8,000 IU/ml. The supernatnat dissolved both a plaminogen-free fibrin plate and a standard fibrin plate. Since the dissolution window formed in the standard fibrin plate was larger than that formed in the plasminogen-free fibrin plate, the supernatant was found to have not only an enzyme activity causing the direct dissolution of fibrin, but also a plasminogen activating effect.

The above-described procedure was repeated by using the dried earthworm powder product M-5 in place of M-4. The results thus obtained were substantially the same as those shown in Table 4.

TABLE 4

Fibrinolytic activity of the supernatant obtained by suspending one part of the dried earthworm powder of the present invention in 10 parts of physiological saline and incubating the suspension at 37° C.

| Incubation period (days) | Fibrinolytic activity (dissolved area of standard fibrin plate, mm$^2$) |
|---|---|
| 0 | 200 |
| 2 | 400 |
| 6 | 717 |
| 10 | 810 |
| 20 | 870 |
| 50 | 1000 |
| 75 | 1100 |

The dried earthworm powder obtained by the process of the present invention, when administered orally to rats and human beings, has an antihyperlipemic effect, a blood sugar lowering effect and a blood pressure regulating effect (i.e., an antihypertensive and/or antihypotensive effect), but the reason for this has not been fully understood. Nevertheless, these effects are believed to be due to the action of the proteolytic enzymes (proteins) contained in the dried earthworm powder, precursors (proteins) of these enzymes, other proteins, lipids or unknown compounds, or a combination thereof. In the most preferred form for use as an antihyperlipemic drug, an antidiabetic drug and a blood pressure regulator (or an antihypertensive and/or antihypotensive drug), the dried earthworm powder of the present invention has a nitrogen content of 7 to 10% and, in other words, a crude protein content of 43.8 to 62.5%.

In one preferred embodiment of the present invention, the earthworm suspension obtained by wet-grinding the earthworms in the above-described Production Process 1 or 2 is then freeze-dried and vacuum-dried as follows.

The suspension obtained by wet-grinding the earthworms is frozen at a temperature of $-10°$ to $-60°$ C., preferably $-30°$ to $-50°$ C., for 5 to 60 hours. Then, while the same temperature is maintained, the frozen suspension is freeze-dried under a vacuum of 0.01 to 0.2 mmHg for 5 to 12 hours. Thereafter, the resulting powder is dried at a temperature of 20° to 30° C. under a vacuum of 0.01 to 0.2 mmHg for 5 to 15 hours. Subsequently, the powder is vacuum-dried at a temperature of 35° to 50° C. for 5 to 10 hours. Thus, there is obtained sterile dried earthworm powder having a moisture content of 5 to 15%. The final stage of the vacuum drying is of the utmost importance. In order to obtain sterile dried earthworm powder without inactivating the proteolytic enzymes, or precursors thereof, present in the dried earthworm powder, the present inveotors have made an intensive study and have found that a proper combination of three factors (i.e., degree of vacuum, temperature and time) is critical in the final stage of the vacuum drying. On the basis of this finding, the above-described operating conditions have been established.

As previously described, it has been reported that six proteolytic enzymes purified from dried earthworm powder (Japanese Patent Laid-Open Nos. 63184/'84 and 184131/'84) are all inactivated by heating at 70° C. for 60 minutes. However, it can be seen from Table 4 that the proteolytic enzymes present in the dried earthworm powder obtained by the process of the present invention are not inactivated.

When some dried earthworm powder products obtained by Production Processes 1 and 2 were preserved in a well-closed state at room temperature (5° to 45° C.) for 5 years, no evidence of physical change or chemical deterioration (such as mold growth) was noted.

The species of earthworm used in the present invention may be selected from various common species including *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima Sieboldi* Horst, *Pheretima hilgendorfi, Pontodrilus matushimensis* Iizuka, *Tubifex hattai* Normura, *Limnodrilus gotoi* Hatai (= *L. socialis* Stephenson) and the like.

When the dried earthworm powder of the present invention is used for purposes of clinical therapy, it may have the form of an oral preparation or a parenteral preparation. However, oral administration of the dried earthworm powder is especially preferred. For oral use, the dried earthworm powder of the present invention may be used alone or in combination with pharmaceutically acceptable carriers to form pharmaceutical preparations such as capsules, tablets, granules, powders, coated tablets, sugar coated tablets and emulsions.

Suitable pharmaceutical carriers include, for example, fillers such as lactose, sucrose, mannitol, glucose, starch, sorbitol, glycine, calcium phosphate and microcrystalline cellulose; binders such as starch, gelatin, acacia, glucose, sucrose, sorbitol, mannitol, tragacanth, hydroxypropylcellulose, hydroxypropoxymethylcellulose, carboxymethylcellulose, 2-methyl-5-vinylpyridine/methyl methacrylate/ethylacrylate copolymer, polyvinylpyrrolidone and sodium alginate; lubricants such as stearic acid, hardened oil, magnesium stearate, calcium stearate, polyoxyethylene monostearate, talc, silicon oxide and polyethylene glycol; disintegrators such as potato starch, and starch containing a surfactant or the like; and humectants such as sodium lauryl sulfate. Where parenteral administration is desired, the dried earthworm powder of the present invention may be used in the form of suppositories. In the case of suppositories, cacao butter, Witepsol, Subanal, polyethylene glycol, polypropylene glycol, glycerogelatin, gelatin capsules and the like can be used as bases. Other additives include well-known safe antiseptics such as methyl p-hydroxybenzoate, propyl p-hydroxybenzoate, butyl p-hydroxybenzoate and butyl hydroxyanisol; and safe colorants.

Where the dried earthworm powder of the present invention is used for the treatment of hyperlipemia or diabetes, its dosage may vary according to the route of administration, the age, body weight and condition of the patient, and the type of the disease. Generally, the preferred daily dose for man ranges from about 0.01 to 5 g. Most preferably, a daily dose of 0.02 to 2 g is given in 1 to 3 divided doses.

Where the dried earthworm powder of the present invention is used for the regulation of blood pressure or for the treatment of hypertension or hypotension, its dosage may vary according to the route of administration, the age, body weight and condition of the patient, and the type of the disease. Generally, the preferred daily dose for man ranges from about 0.01 to 3 g. Most preferably, a daily dose of 0.02 to 2 g is given in 1 to 3 divided doses.

EFFECTS

The procedure and results of toxicity tests of the dried earthworm powder of the present invention and the procedures and results of pharmacological tests thereof for antihyperlipemic, antidiabetic (or hypoglycemic) and antihypertensive (or hypotensive) effects will be described in detail hereinbelow.

A. Acute Toxicity Tests

Acute toxicity tests was carried out by administering the dried earthworm powder of the present invention orally. In these tests, male mice of the ddy strain, weighing 30±2 g, and male rats of the Wistar strain, weighing 100±2 g, were used in groups of five. The test samples were the aforesaid dried earthworm powder products M-1 (having a moisture content of 10.2%, an ash content of 5.1% and a nitrogen content of 9.4%), M-2 (having a moisture content of 10.4%, an ash content of 5.3% and a nitrogen content of 8.6%), M-3 (having a moisture content of 10.7%, an ash content of 5.2% and a nitrogen content of 9.2%), M-4 (having a moisture content of 10.6%, an ash content of 5.6% and a nitrogen content of 9.6%), M-5 (having a moisture content of 9.5%, an ash content of 4.5% and a nitrogen content of 7.8%) and M-6 (having a moisture content of 9.2%, an ash content of 4.7% and a nitrogen content of 8.4%). Using a probang, each of the test samples was forcibly administered to the aforesaid mice and rats in varying doses of 0.1 to 5 g/kg for mice and 2 to 8 g/kg for rats. During the test period, the animals were placed in a room maintained at 22° to 23° C. and observed for 14 days after administration. No death occurred at the doses employed for these tests. The behavior of the animals was observed from time to time to see if poinsoning had occurred, but no difference was recognized between the test groups and the normal control group. Moreover, there was no appreciable difference in weight gain between the test groups and the normal control group. Autopsies were carried out at the end of the tests, but revealed no macroscopic changes in any of the principal organs. Thus, the dried earthworm powder of the present invention has such low toxicity that it was possible to determined its $LD_{50}$ value.

B. Effect on Rats with Experimentally Induced Hyperlipemia

Pharmacological Test 1

(1) Animals:

Male rats of the Wistar strain, weighing 100±1 g, were used in groups of eight.

(2) Diets:

A high-cholesterol diet was prepared by adding 1% by weight of cholesterol and 0.5% by weight of cholic acid to a powder feed (CE-2; manufactured by Nippon Clea Co.) and blending them well. Then, two test diets were prepared by blending this high-cholesterol diet with 2% of each of two dried earthworm powder products obtained in accordance with the present invention [i.e., M-2 (having a moisture content of 10.4%, an ash content of 5.3% and a nitrogen content of 8.6%) and M-5 (having a moisture content of 9.5%, an ash content of 4.5%, and a nitrogen content of 7.8%)].

(3) Experimental conditions:

The rats were placed in separate cages and fed ad libtum with each diet and water. They were maintained at a constant temperature of 23°±1° C. and a constant relative humidity of 55±5% for 7 days. After 7 days, they were deprived of food (but allowed to drink water) overnight and then anesthetized with pentobarbital sodium (trade name: Nembutal). A blood sample was collected from the abdominal descending aorta and centrifuged under refrigerated conditions to obtain serum. The levels of TC, free cholesterol (hereinafter referred to as FC), LDL-C and HDL-C in the serum were determined by using Toshiba TBA-480 Automatic Analyzer and TA480 Test Reagents commercially available from Wako Pure Chemicals Co., Ltd. AI was calculated from the data thus obtained.

(4) Results

The results thus obtained are shown in Table 5.

TABLE 5

|  | High-chloesterol diet group | M-2 containing diet group | M-2 containing diet group |
| --- | --- | --- | --- |
| Dose (wt. %) |  | 2 | 2 |
| Number of rats | 8 | 8 | 8 |
| (Serum levels) |  |  |  |
| TC (mg/dl) | 325.5 ± 20.8[a] | 185.4 ± 10.7***[b] | 186.8 ± 10.6***[b] |
| FC (mg/dl) | 70.4 ± 5.2 | 44.8 ± 2.5** | 42.2 ± 2.4** |
| LDL-C (mg/dl) | 229.8 ± 22.5 | 113.6 ± 7.7** | 113.0 ± 7.6** |
| HDL-C (mg/dl) | 31.6 ± 4.3 | 30.5 ± 2.3 | 30.7 ± 2.7 |
| AI | 10.21 ± 2.42 | 5.52 ± 0.94* | 5.55 ± 0.98* |

[a]Each value indicates a mean ± standard deviation (S.D.) for 8 rats.
[b]Statistical significance as compared with the values of the cholesterol-rich group: *$P < 0.05$, $P < 0.01$, *$P < 0.001$.

In the groups fed on the diet containing 2% of the dried earthworm powder of the present invention, the serum TC, FC, LDL-C and AI levels showed statistically significantly reductions, but no significant change in HDL-C was observed.

Thus, the dried earthworm powder of the present invention was found to have an excellent antihyperlipemic effect.

Pharmacological Test 2

(1) Animals:

Male rats of the Sprague-Dawley strain (hereinafter referred to as the SD strain), weighing 105±1 g, were used in groups of eight.

(2) Diets:

The high-cholesterol diet used in pharmacological test 2 had the composition shown in Table 6.

TABLE 6

| Ingredient | % by weight |
| --- | --- |
| Cholesterol | 0.5 |
| Cholic acid | 1.0 |
| Casein | 20.0 |
| Sucrose | 50.5 |
| Hardened coconut oil | 12.0 |
| Cellulose | 4.0 |
| Salt mixture[a] | 4.0 |
| Vitamin mixture[b] | 0.5 |
| White fish meal | 7.5 |

(Note)
[a,b]The compositions of the salt mixture and vitamin mixture are described in Fukushima et al., Japanese Journal of Pharmacy, Vol. 89, pp. 857-862 (1962).

The ingredients listed in Table 6 were blended well to prepare a high-cholesterol diet. Then, test diets were prepared by blending this high-cholesterol diet with 0.25% by weight of the dried earthworm powder product M-3 obtained in accordance with the present invention (having a moisture content of 10.7%, an ash content of 5.2% and a nitrogen content of 9.2%), 0.5% by weight of the dried earthworm powder product M-1 obtained in accordance with the present invention (having a moisture content of 10.2%, an ash content of 5.1% and a nitrogen content of 9.4%), 0.5 or 1.0% by weight of γ-oryzanol (trade name: Hizet Fine Granules) as a control drug, or 1.0% by weight of soysterol (trade name: Moristerol Fine Granules) as a control drug.

(3) Experimental conditions:

The rats were placed in separate cages by twos and fed ad libtum with each diet and water. They were maintained at a constant temperature of 23°±1° C. and a constant relative humidity of 55±5% for 4 weeks. After 4 weeks, they were deprived of food (but allowed to drink water) overnight and then anesthetized with pentobarbital sodium (trade name: Nembutal). A blood sample was collected from the abdominal descending aorta and centrifuged under refrigerated conditions to obtain serum.

The levels of TC, FC, TG, PL, free fatty acids (hereinafter referred to as NEFAs), LDL-C, AI, glutamic oxaloacetic transaminase (hereinafter referred to as GOT) and glutamic pyruvic transaminase (hereinafter referred to as GPT) in the serum were determined (or calculated) by using Toshiba TBA-480 Automatic Analyzer and TA480 Test Reagents commercially available from Wako Pure Chemicals Co., Ltd. Liver lipids were extracted according to Folch's method and the levels of TC, TG and PL in the liver lipids were determined in the same manner as described above.

(4) Results:

Table 7 shows the results of the experiment in which the effect of the dried earthworm powder of the present invention on rats with experimentally induced hyperlipemia was tested in comparison with two control drugs (i.e., γ-oryzanol and isosterol). In both groups fed with the diets containing 0.25 or 0.5% of the dried earthworm powder of the present invention, the serum TC, FC, PL and NEFA levels showed a statistically significant reduction, as compared with the high-cholesterol diet group. The serum TG level tended to lower, but no significant reduction was observed.

The diets containing 0.5 or 1% of γ-oryzanol caused a significant reduction in NEFA, but no significant lowering of TC, FC, TG or PL was observed. On the other hand, the diet containing 1% of soysterol as a control drug caused a significant reduction in TC, FC and PL, but the TG and NEFA levels were substantially the same as those of the high-cholesterol diet group.

As described above, HDL-C is considered to be an arteriosclerosis-improving factor, and many investigators in basic and clinical fields of medicine have demonstrated that an elevation in HLD-C is a useful criterion for the evaluation of antihyperlipemic drugs. It can be seen from Table 7 that the groups fed with the diets containing the dried earthworm powder of the present invention showed a statistically significant elevation in HDL-C, as compared with the high-cholesterol diet group. In constrast, γ-oryzanol used as a control drug failed to elevate HDL-C. However, soysterol caused a significant elevation in HDL-C.

As described above, the effect of lowering AI is important for antihyperlipemic drugs. It was demonstrated that the groups fed with the diets containing the dried earthworm powder of the present invention or soysterol as a control drug showed a significant reduction in AI. However, in the groups fed with the diets containing γ-oryzanol as a control drug, AI showed a lowering tendency, but no significant reduction was observed.

As described above, commercially available antihyperlipemic drugs may cause hepatic disorders as siede effects. Accordingly, this poses a problem in their prolonged use. In order to examine the influence of the test drugs on the liver, the serum GOT and GPT levels were determined. It is generally known that an elevation in these parameters suggest a hepatic functional disorder. The group fed with the diet containing the dried earthworm powder of the present invention showed a significant reduction in both GOT and GPT, as compared with the high-cholesterol diet group. In constrast, the group fed with the diet containing 0.5% of γ-oryzanol as a control drug showed a distinct, though not significant, elevating tendency and the group fed with the diet containing 1% of γ-oryzanol showed a statistically significant elevation in both GOT and GPT. In this respect, the group fed with the diet containing 1% of soysterol as a control drug showed lower GOT and GPT levels than the high-cholesterol diet group, but this reduction was not statistically significant.

With regard to liver weight, the dried earthworm powder containing diet groups showed a significant decrease, as compared with the high-cholesterol diet group. However, little difference was recognized between the γ-oryzanol and soysterol containing diet groups and the high-cholesterol diet group.

With regard to TC present in the liver lipids, both the dried earthworm powder containing diet groups and the two control drug containing diet groups showed a significant reduction, as compared with the high-cholesterol diet group.

With regard to TG present in the liver lipids, both the dried earthworm powder containing diet groups and the two control drug containing diet groups showed a slight lowering tendency, but no essential change was recognized.

With regard to PL present in the liver lipids, the dried earthworm powder containing diet groups showed a significant reduction, as compared with the high-cholesterol diet group. However, no change was recognized in the two control drug containing diet groups.

In both the dried earthworm powder containing diet groups and the two control drug containing diet groups, the body weight of the rats increased steadily without showing any significant variation.

TABLE 7

| Type of diet | Normal diet group | High-cholesterol diet group | Dried earthworm powder containing diet group | |
|---|---|---|---|---|
| Dose (wt. %) | | | 0.25 | 0.5 |
| Number of rats | 8 | 8 | 8 | 8 |
| Serum | | | | |
| TC (mg/dl) | 50.4 ± 2.5*** | 420.2 ± 45.3$^a$ | 195.7 ± 18.1***$^b$ | 188.7 ± 19.2*** |
| FC (mg/dl) | 11.0 ± 0.9*** | 100.3 ± 11.8 | 42.6 ± 3.7*** | 42.2 ± 4.8*** |
| TG (mg/dl) | 57.6 ± 7.9 | 83.4 ± 12.2 | 68.1 ± 4.1 | 60.3 ± 10.2 |
| PL (mg/dl) | 96.2 ± 3.8*** | 176.1 ± 14.2 | 114.8 ± 4.6*** | 116.5 ± 7.1*** |
| NEFA (mEq/l) | 0.768 ± 0.022** | 1.043 ± 0.074 | 0.773 ± 0.049* | 0.681 ± 0.062** |
| HDL-C (mg/dl) | 28.5 ± 2.0*** | 16.4 ± 1.7 | 22.4 ± 0.8* | 22.7 ± 0.9* |
| AI | 0.81 ± 0.12 | 29.69 ± 5.52 | 8.07 ± 1.84** | 7.75 ± 2.12** |
| GOT (U/l) | 70.4 ± 5.4*** | 372.3 ± 54.7 | 136.7 ± 20.4*** | 97.4 ± 3.8*** |
| GPT (U/l) | 28.8 ± 2.5*** | 180.7 ± 27.8 | 61.8 ± 14.0** | 38.9 ± 2.7** |
| Liver | | | | |
| Weight (g) | 9.2 ± 0.3*** | 13.6 ± 0.3 | 11.3 ± 0.3** | 10.4 ± 0.5*** |
| TC (mg/g) | 2.8 ± 0.2*** | 40.2 ± 0.9 | 30.6 ± 1.2*** | 19.8 ± 1.1*** |
| TG (mg/g) | 6.6 ± 1.0 | 7.5 ± 0.3 | 6.5 ± 0.6 | 7.0 ± 0.6 |
| PL (mg/g) | 13.1 ± 0.3*** | 24.0 ± 0.4 | 20.7 ± 0.3*** | 16.9 ± 0.4*** |
| Body weight (g) | | | | |
| Initial | 105.2 ± 1.0 | 105.2 ± 1.0 | 105.4 ± 1.1 | 10.52 ± 1.0 |
| Final | 286.8 ± 5.8 | 252.6 ± 5.5 | 259.2 ± 6.2 | 259.7 ± 7.6 |

| Type of diet | γ-Oryzanol containing diet group | | Soysterol containing diet group |
|---|---|---|---|
| Dose (wt. %) | 0.5 | 1.0 | 1.0 |
| Number of rats | 8 | 8 | 8 |
| Serum | | | |
| TC (mg/dl) | 328.7 ± 39.5 | 307.4 ± 42.3 | 194.3 ± 19.0*** |
| FC (mg/dl) | 84.3 ± 9.2 | 71.8 ± 9.1 | 42.4 ± 5.8** |
| TG (mg/dl) | 67.4 ± 11.4 | 56.9 ± 5.5 | 80.7 ± 10.0 |
| PL (mg/dl) | 163.9 ± 12.3 | 151.2 ± 9.7 | 143.5 ± 9.9* |
| NEFA (mEq/l) | 0.688 ± 0.062** | 0.799 ± 0.060* | 1.031 ± 0.058 |
| HDL-C (mg/dl) | 18.0 ± 2.8 | 16.5 ± 0.8 | 21.8 ± 0.9* |
| AI | 19.86 ± 4.82 | 18.44 ± 4.32 | 8.82 ± 2.20** |
| GOT (U/l) | 475.8 ± 77.1 | 618.4 ± 94.8* | 246.4 ± 33.8 |
| GPT (U/l) | 249.7 ± 35.4 | 328.7 ± 72.7* | 107.2 ± 16.5 |
| Liver | | | |
| Weight (g) | 13.8 ± 0.4 | 12.8 ± 0.5 | 13.2 ± 0.4 |
| TC (mg/g) | 34.2 ± 1.3** | 32.8 ± 0.9*** | 34.3 ± 1.3** |
| TG (mg/g) | 6.5 ± 0.6 | 6.5 ± 0.6 | 7.1 ± 0.6 |
| PL (mg/g) | 23.1 ± 0.9 | 23.2 ± 0.6 | 23.0 ± 0.6 |
| Body weight (g) | | | |
| Initial | 105.1 ± 1.0 | 105.4 ± 1.0 | 105.3 ± 1.0 |
| Final | 256.4 ± 8.7 | 256.2 ± 10.8 | 258.4 ± 7.0 |

$^a$Each value indicates a mean ± standard deviation (S.D.) for 8 rats.
$^b$Statistical significance as compared with the values of the high-cholesterol diet group: *P < 0.05, P < 0.01, *P < 0.001.

C. Oral Administration of Dried Earthworm Powder to Human Subjects with Hyperlipemia To 4 volunteers who consented to this experiment, capsules D (each containing 150 mg of the previously described M-2 having a moisture content of 10.4%, an ash content of 5.3% and a nitrogen content of 8.6%) prepared in the manner described in Example 10 given later were administered orally. The dosage was such that one capsule was given three times a day within 30 minutes after each meal. The administration was continued for a period of 6 or 7 months and, in principle, the serum levels of lipids were determined at intervals of 3 or 4 months after commencement of the administration. To this end, a blood sample was collected early in the morning while the stomach was empty, and tested for serum TC, TG, HDL-C and AI levels. The determinations were made using the previously described kits commercially available from Wako Pure Chemicals Co., Ltd. The results thus obtained are shown in Table 8.

TABLE 8

| Y.I. (female, aged 80) | | | | | | |
|---|---|---|---|---|---|---|
| | Before administration | After 1 month | After 3 months | After 4 months | After 6 months | After 7 months |
| TC (mg/dl) | 280.7 | 240.3 | 227.6 | 218.2 | 184.7 | 186.6 |
| TG (mg/dl) | 119.2 | 110.0 | 70.9 | 94.6 | 106.3 | 97.5 |
| HDL-C (mg/dl) | 36.0 | 36.7 | 36.0 | 36.5 | 37.4 | 38.3 |
| AI | 6.80 | 5.54 | 5.32 | 4.98 | 3.94 | 3.87 |

| S.I. (female, aged 62) | | | |
|---|---|---|---|
| | Before administration | After 4 months | After 6 months |
| TC (mg/dl) | 239.6 | 206.2 | 197.2 |
| TG (mg/dl) | 92.5 | 92.0 | 90.1 |
| HDL-C (mg/dl) | 45.2 | 42.7 | 46.4 |
| AI | 4.30 | 3.83 | 3.25 |

| A.K. (male, aged 55) | | | |
|---|---|---|---|
| | Before administration | After 3 months | After 6 months |
| TC (mg/dl) | 264.7 | 220.4 | 209.4 |
| TG (mg/dl) | 125.4 | 122.4 | 92.8 |
| HDL-C (mg/dl) | 47.2 | 46.4 | 52.6 |
| AI | 4.61 | 3.75 | 2.98 |

| G.K. (male, aged 62) | | | |
|---|---|---|---|
| | Before administration | After 3 months | After 6 months |
| TC (mg/dl) | 238.4 | 194.8 | 174.7 |
| TG (mg/dl) | 116.6 | 99.5 | 83.7 |
| HDL-C (mg/dl) | 56.5 | 52.3 | 57.4 |
| AI | 3.22 | 2.72 | 2.04 |

For healthy inhabitants of the district where this experiment concerning the administration of the dried earthworm powder of the present invention to 4 volunteers was carried out, the normal serum lipid values are 130–230 mg/dl for TC, 50–170 mg/dl for TG, and 35–60 mg/dl for HDL-C. It can be seen from Table 8 that, in all of the four subjects, the TC level before commencement of the treatment exceeded its normal range. The TG and HDL-C levels were within their normal ranges.

Although the results shown in Table 8 were obtained from the oral administration of dried earthworm powder to only 4 volunteers, the TC levels of 238–280 mg/dl before commencement of the treatment were reduced to 194–220 mg/dl (within the normal range) after 3 or 4 months of treatment, and markedly reduced to 174–209 mg/dl after 6 or 7 months. The AI value began to lower distinctly after 3 or 4 months of treatment. After 6 or 7 months, a marked reduction in AI was observed together with the reduction in TC.

On the other hand, the HDL-C level remained almost constant and showed no appreciable change. However, a slight but distinct rising tendency was observed after 6 or 7 months. The TG level tended to lower after 3 or 4 months and showed a distinct reduction after 6 or 7 months.

In this experiment concerning the oral administration to human subjects, a marked reduction in TC and AI and a slight elevation in HDL-C were observed, as was the case with the experiment concerning the oral administration to rats with experimentally induced hyperlipemia. However, in contrast to the oral administration to rats with experimentally induced hyperlipemia in which no significant reduction in TG was observed, the oral administration to human subjects caused a distinct reduction in TG after 6 or 7 months. This is considered to be a noteworthy result.

This experiment concerning the oral administration of dried earthworm powder to human subjects could be completed in safety and without producing any side effects. For example, even prolonged administration over a period of 6 or 7 months involved no risk of causing hypoglycemia in which blood sugar would be reduced to a level below the lower limit of its normal range (60 to 110 mg/dl). As can be seen from Table 8, the dried earthworm powder is not an antihperlipemic drug which, like drugs comprising synthetic organic compounds, can achieve the intended purpose quickly in a relatively short period of time. That is, the dried earthworm powder is thought to be a slow-acting antihyperlipemic drug which requires continued administration for a relatively long period of time. However, when the dried earthworm powder was administered to human subjects, TC and AI began to lower distinctly after 3 or 4 months. Moreover, HDL-C showed a slight rising tendency after 6 or 7 months and TG showed a distinct reduction after 6 or 7 months.

No particular limitation is placed on the age of the patient to whom the dried earthworm powder of the present invention is applied. Although the dried earthworm powder of the present invention is of the universal type, it should preferably be applied to patients of middle or advanced age. On the basis of the above-described results, the dried earthworm powder of the present invention has been found to be a safe and effective remedy and preventive for hyperlipemia.

D. Effect on Mice with Experimentally Induced Diabetes: Pharmacological Test 3

(1) Animals

Male mice of the ddy strain, weighing 30±2 g, were used in groups of five.

(2) Food and experimental conditions

A solid food commercially available from Nippon Clea Co. was used in this test. The mice were placed in separate cages and fed ad libtum with the food and water. They were maintained at at a constant temperature of 23°±1° C. and a constant relative humidity of 55±5%.

The aforesaid male mice of the ddy strain were fasted for 16 hours and then treated by intravenous injection of 75 mg/kg of alloxan. After 48 hours, an aqueous suspension of the dried earthworm powder of the present invention was orally administered thereto in a dose of 300 mg/kg. For this purpose, the dried earthworm powder products M-1 (having a moisture content of 10.2%, an ash content of 5.1% and a nitrogen content of 9.4%), M-2 (having a moisture content of 10.4%, an ash content of 5.3% and a nitrogen content of 8.6%), M-3 (having a moisture content of 10.7%, an ash content of 5.2% and a nitrogen content of 9.2%), M-4 (having a moisture content of 10.6%, an ash content of 5.6% and a nitrogen content of 9.6%), M-5 (having a moisture content of 9.5%, an ash content of 4.5% and a nitrogen content of 7.8%) and M-6 (having a moisture content of 9.2%, an ash content of 4.7% and a nitrogen content of 8.4%) were used as test samples. After 150 minutes, a blood sample was collected by heart puncture and its blood sugar level was determined by the glucose oxidase method.

The results of the determinations are shown in Table 9. Thus, the dried earthworm powder of the present invention was found to be capable of lowering blood sugar to a statistically significant degree.

TABLE 9

| Dried earthworm powder of the invention | Blood sugar level (mg/dl), mean ± standard deviation |
|---|---|
| None (control) | 474 ± 29 |
| M-1 | 381 ± 39** |
| M-2 | 354 ± 45** |
| M-3 | 377 ± 35** |
| M-4 | 342 ± 32*** |
| M-5 | 378 ± 36** |
| M-6 | 383 ± 27** |

*P < 0.05;
**P < 0.01;
***P < 0.001.

E. Experiment on Oral Administration of Dried Earthworm Powder to Human Subject with Diabetes To 5 volunteers who consented to this experiment, capsules C prepared in Example 6 given later (each containing 150 mg of the dried earthworm powder product M-3 having a moisture content of 10.7%, an ash content of 5.2% and a nitrogen content of 9.2%) was orally administered in combination with alimentotherapy. The doasage was such that one capsule was given three times a day within 30 minutes after each meal. In a male subject aged 62 years, the treatment was continued for 9 months and blood samples were collected at intervals of one month. In a male subject aged 59 years, blood samples were collected before treatment and after 2, 3 and 4 months of treatment. In a female subject aged 76 years, blood samples were collected before treatment and after 4 months of treatment, and in a female subject aged 79 years, blood samples were collected before treatment and after 3 and 6 months of treatment. In a female subject aged 61 years, blood samples were collected before treatment and after 1, 3, 4 and 8 months of treatment. Blood sugar levels were determined according to the glucose oxidase method. The results thus obtained are shown in Table 10.

TABLE 10

Blood sugar level (mg/dl)

S.T. (male, aged 62)

| | Before treatment | After 1 month | After 2 months | After 3 months | After 4 months | After 5 months | After 6 months | After 7 months | After 8 months | After 9 months |
|---|---|---|---|---|---|---|---|---|---|---|
| Before breakfast | 124 | 101 | 90 | 93 | 95 | 85 | 90 | 90 | 80 | 90 |
| 2 hours after breakfast | 179 | 169 | 154 | 135 | 132 | 127 | 130 | 128 | 102 | 129 |
| Before lunch | 133 | 130 | 110 | 102 | 100 | 99 | 92 | 98 | 90 | 97 |
| 2 hours after lunch | 271 | 220 | 133 | 135 | 140 | 132 | 128 | 130 | 105 | 110 |
| Before supper | 225 | 196 | 108 | 105 | 98 | 100 | 105 | 99 | 95 | 98 |
| 2 hours after supper | 270 | 220 | 202 | 185 | 150 | 148 | 145 | 143 | 130 | 132 |

| | K.K. (male, aged 59) | | | K.M. (female, aged 79) | | | T.Z. (female, aged 76) | |
|---|---|---|---|---|---|---|---|---|
| | Before treatment | After 2 months | After 3 months | After 4 months | Before treatment | After 3 months | After 6 months | Before treatment | After 4 months |
| Before breakfast | 205 | 198 | 100 | 92 | 149 | 95 | 97 | 115 | 81 |
| 2 hours after breakfast | 282 | 156 | 150 | 146 | 302 | 130 | 107 | 155 | 95 |
| Before lunch | 138 | 126 | 114 | 94 | 172 | 95 | 80 | 148 | 95 |
| 2 hours after lunch | 283 | 262 | 117 | 150 | 196 | 171 | 104 | 127 | 119 |
| Before supper | 170 | 280 | 83 | 91 | 127 | 107 | 91 | 127 | 96 |
| 2 hours after supper | 304 | 324 | 152 | 149 | 142 | 99 | 116 | 114 | 112 |

| | K.K. (female, aged 61) | | | | |
|---|---|---|---|---|---|
| | Before treatment | After 1 month | After 3 months | After 4 months | After 8 months |
| Before breakfast | 129 | 162 | 74 | 79 | 89 |
| 2 hours after breakfast | 282 | 241 | 230 | 220 | 197 |
| Before lunch | 265 | 188 | 256 | 228 | 210 |
| 2 hours after lunch | 393 | 325 | 325 | 152 | 141 |
| Before supper | 378 | — | 221 | 141 | 100 |
| 2 hours after supper | 390 | — | 251 | 166 | 143 |

For healthy inhabitants of the district in which this experiment was carried out, the normal blood sugar levels were 50–100 mg/dl before breakfast, 150 mg/dl or less two hours after breakfast, 50–100 mg/dl before lunch, 150 mg/dl or less two hours after lunch, 50–100 mg/dl before supper, and 150 mg/dl or less two hours after supper. Before commencement of the treatment, all of the five subjects listed in Table 10 showed a high blood sugar level before breakfast (i.e., at the time of hunger) and, therefore, were diabetic patients.

The male subject aged 62 years, who was thought to have a moderate degree of diabetes, began to show an improvement in blood sugar level after 2 months of treatment with the dried earthworm powder of the present invention. After 3 months of treatment, five test values were restored to near normal levels, though the test value two hours after supper was as high as 185 mg/dl. After 4 months of treatment, all of the six test values returned to their normal levels. Thereafter, the six test values for blood sugar were maintained within their normal ranges for 5 months.

In the male subject aged 59 years, five test values returned to their normal levels after 3 months of treatment, though the test value before supper was slightly higher (114 mg/dl). After 4 months of treatment, all of the six test values came within their normal ranges.

In the female subject aged 79 years, four test values were restored to their normal levels after 3 months of treatment, though the test values two hours after lunch and before supper were slightly higher (171 mg/dl and 107 mg/dl). After 6 months of treatment, all of the six test values were completely restored to their normal levels.

In the female subject aged 76 years, who was a patient with mild diabetes, the six test values for blood sugar returned to their normal levels after 4 months of treatment.

The female subject aged 61 years was a patient with a relatively severe degree of diabetes. After 4 months of treatment with the dried earthworm powder of the present invention, the subject began to show an improvement in blood sugar level. After 8 months, four test values were restored to their normal levels, though the test values two hours after breakfast and before lunch were as high as 197 mg/dl and 210 mg/dl, respectively.

This experiment concerning the oral administration of dried earthworm powder to human subjects could be completed in safety and without producing any side effects. For example, even prolonged administration over a period of 6 to 9 months involved no risk of causing hypoglycemia in which blood sugar would be reduced to a level below the lower limit of its normal range. Thus, the dried earthworm powder of the present invention was found to be a safe drug.

The above-described results can be summarized as follows: When the dried earthworm powder of the present invention was orally administered to a patient with a severe degree of diabetes, it was somewhat difficult to restore all of the six test values for blood sugar to their normal levels. After 8 months of treatment, however, an improvement was achieved in that four of the six test values were restored to their normal levels. In the case of patients with a mild or moderate degree of diabetes, all of the test values could be restored to their normal levels after 4 months of treatment and thenceforward. Thus, the dried earthworm powder of the present invention has been found to be a safe and excellent hypoglycemic drug which is useful for the treatment and prevention of diabetes.

F. Effect on Spontaneous Hypertensive Rats (SHRs)

Pharmacological Test 4

(Hypotensive Effect and Heart Rate Increase in SHRs)

To 10- to 12-weeks-old male SHRs (weighing 200 to 300 g and having a blood pressure of 150 to 200 mmHg) fasted for a whole day and night, a suspension of a test sample (i.e., dried earthworm powder M-4) in a 0.5% aqueous solution of carboxymethylcellulose was orally administered in a dose of 100 mg/kg. (The dose of hydralazine hydrochloride used as a control drug was 10 mg/kg.) Blood pressure measurements were made after 0, 1, 2, 4 and 6 hours. (The results are expressed as the mean of 3 or 4 measurements.) Thus, the hypotensive effect of the test sample and the heart rate increase caused thereby were evaluated by comparing the blood pressure and heart rate before administration of the test sample, with the blood pressure and heart rate after administration of the test sample.

Blood pressure measurements were made in the following manner: The SHR was previously warmed to 45°–50° C., for about 5 minutes, and the systolic pressure of its caudal artery was non-surgically measured by tail plethysmography using an automatic blood pressure recorder [The Journal of Laboratory and Clinical Medicine, Vol. 78, p. 957 (1971)]. The results thus obtained are shown in Table 11.

The hypotensive effect is expressed in terms of the maximum reduction from the systolic pressure observed before administration. When the dried earthworm powder products M-2 and M-4 obtained by Production Process 1 and the dried earthworm products M-2 and M-4 obtained by Production Process 2 were orally administered to SHRs in a dose of 100 mg/dl, a maximum hypotensive effect was observed 1 to 2 hours after administration. That is, the dried earthworm powder reduced the blood pressure of the SHRs by 28 to 35 mmHg and this effect lasted 6 hours.

The results of measurement of heart rate increase are also shown in Table 11. It was found that, unlike hydralazine hydrochloride used as a control drug, none of the test samples of dried earthworm powder exerted undesirable side effects (such as tachycardia) on the heart.

TABLE 11

| Test sample | Hypotensive effect on SHRs ($-\Delta$, mmHg) | Heart rate increase (beats/minute) |
|---|---|---|
| (Dried earthworm powder) | | |
| M-2 | 33 | 18 |
| M-4 | 35 | 19 |
| M-5 | 28 | 22 |
| M-6 | 31 | 20 |
| (Control) | | |
| Hydralazine hydrochloride | 60 | 85 |

G. Hemolytic Effect

Pharmacological Test 5

In this test, the dried earthworm powder products M-2 and M-4 obtained by Production Process 1 and the dried earthworm powder products M-5 and M-6 obtained by Production Process 2 were used as test samples. Specifically, 1 part by weight of each test sample was added to 5 parts by weight of physiological saline and suspended well therein. The resulting suspension was allowed to stand in a refrigerator at 5° C. for 24 hours and then filtered under reduced pressure. The filtrate was regarded as a water extract.

Ethyl alcohol and acetone extracts were prepared by adding 5 parts by weight of ethyl alcohol or acetone to 1 part by weight of each of the four test samples and suspending the latter well in the former. The resulting suspension was allowed to stand at 15°–20° C. for 24 hours and then filtered under reduced pressure. The filtrate was evaporated to dryness at 40°–45° C. The resulting residue was dissolved in physiological saline containing 1% carboxymethylcellulose to prepare a 30% solution. Hemolytic effect was evaluated in the following manner: Blood was collected from an auricular vein of a mature rabbit weighing about 3 kg, and subjected to a defibrination treatment. Each of the aforesaid water, ethyl alcohol and acetone extracts was diluted with physiologocal saline to concentrations of 5, 1, 0.1, 0.01, 0.001 and 0.0001% by weight. These solutions were placed in 5 ml test tubes, and one drop of the defibrinated blood was added to each test tube with a pipet. After an hour, the test tubes were examined for hemolysis. The test results thus obtained are shown in Table 12, indicating that none of the test samples of dried earthworm powder caused hemolysis at any concentration.

TABLE 12

| Extract of dried earthworm powder | Concentration (wt. %) | | | | | |
|---|---|---|---|---|---|---|
| | 5 | 1 | 0.1 | 0.01 | 0.001 | 0.0001 |
| Water extract | — | — | — | — | — | — |
| Ethyl alcohol extract | — | — | — | — | — | — |
| Acetone extract | — | — | — | — | — | — |

It has been reported in the literature that dried earthworms ("dilong") have a toxic effect characterized by hemolysis, i.e., destruction of red blood cells [Shinryu Ofuchi, "Mimizu-to-Jinsei (Earthworms and Human Life)", Maki Shobo, Oct. 30, 1947, pp. 223-226; Nikiji Hatai "Mimizu (Earthworms), Reprinted Edition)", Scientist Co., Apr. 30, 1980, pp. 160-163]. It has also been reported that water or ethyl alcohol extracts of dried earthworms ("dilong") have a partial hemolytic effect [Kenjiro Ikawa, Yamaguchi Igaku, Vol. 9, pp. 571-576 (1960)]. However, it has been found that the dried earthworm powder obtained by the process of the present invention does not have such a hemolytic effect.

H. Oral Administration of Dried Earthworm Powder to Human Subjects with Hypertension or Hypotension To 14 volunteers (7 males and 7 females) who included 8 hypertensive patients (4 males and 4 females) and 6 hypotensive patients (3 males and 3 females) and consented to this experiment, the dried earthworm powder of the present invention was administered orally. For this purpose, capsules A prepared in Example 4 given later (each containing 150 mg of the dried earthworm powder product M-2 having a moisture content of 10.4%, an ash content of 5.3% and a nitrogen content of 8.6%), capsules E prepared in Example 11 given later (each containing 150 mg of the dried earthworm powder product M-4 having a moisture content of 10.6%, an ash content of 5.6% and a nitrogen content of 9.6%) and capsules F prepared in Example 12 given later (each containing 150 mg of the dried earthworm powder product M-5 having a moisture content of 9.5%, an ash content of 4.5% and a nitrogen content of 7.8%) were used. The dosage was such that one capsule was given three times a day within 30 minutes after each meal. The oral administration was continued for a period of 2 to 11 months, during which the patients were observed at intervals of 1 to 2 weeks for the first 2 months and thereafter at intervals of 1 month. The results thus obtained are shown in Table 13. When the dried earthworm powder of the present invention was administered to hypertensive patients, the maximum and minimum blood pressures were both reduced by about 30 mmHg. More specifically, the maximum blood pressure of the hypertensive patients was reduced by 30 to 39 mmHg and the minimum blood pressure thereof was reduced by 26 to 34 mmHg. Once the blood pressure returned to its normal levels, they were maintained for 3 to 7 months. On the other hand, when dried earthworm powder of the present invention was administered to hypotensive patients, the blood pressure was elevated by 15 to 30 mmHg. More specifically, the maximum blood pressure of the hypotensive patients was elevated by 20 to 30 mmHg and the minimum blood pressure thereof was elevated by 15 to 22 mmHg. Once the blood pressure returned to its normal levels, they were maintained for 3 to 5 months. Although the capsules containing the dried earthworm powder of the present invention were administered for long periods of 2 to 11 months, neither abnormal reduction nor abnormal elevation in blood pressure occurred, and other side effects were not observed at all.

Thus, it has been found that blood pressure regulator preparations, or antihypertensive and/or antihypotensive preparations, containing the dried earthworm powder of the present invention as the active ingredient have a mild hypotensive and/or hypertensive effect on human beings to bring about a gentle reduction and/or elevation in blood pressure and, therefore, can be safely used for a long period of time not only for the treatment of hypertension and hypotension but also for the prevention thereof.

TABLE 13

| Patient | | | Blood Pressure before treatment (mmHg) | | Treatment | | Blood pressure after treatment (mmHg) | | Observation period (months) | After discontinuance of treatment | |
|---|---|---|---|---|---|---|---|---|---|---|---|
| | | | | | | | | | | Blood pressure (mmHg) | |
| Name | Sex | Age | Maximum blood pressure | Minimum blood pressure | Type of capsule | Period (months) | Maximum blood pressure | Minimum blood pressure | | Maximum blood pressure | Minimum blood pressure |
| K.H. | Male | 57 | 165 | 110 | A | 2 | 133 | 84 | 7 | 135 | 83 |
| T.S. | Male | 62 | 169 | 110 | E | 10 | 132 | 82 | 6 | 130 | 85 |
| F.H. | Male | 58 | 167 | 115 | F | 4 | 131 | 85 | 7 | 132 | 85 |
| K.S. | Male | 70 | 172 | 118 | E | 10 | 136 | 84 | 3 | 134 | 82 |
| Y.S. | Female | 69 | 167 | 114 | A | 8 | 132 | 80 | 4 | 130 | 83 |
| I.S. | Female | 62 | 165 | 112 | E | 9 | 135 | 83 | 6 | 132 | 80 |
| A.M. | Female | 79 | 176 | 120 | F | 11 | 137 | 88 | 4 | 136 | 86 |
| S.Y. | Female | 73 | 162 | 116 | E | 9 | 132 | 86 | 3 | 134 | 82 |
| I.Y. | Male | 42 | 102 | 65 | A | 6 | 132 | 80 | 5 | 130 | 76 |
| N.K. | Male | 36 | 100 | 52 | E | 10 | 125 | 74 | 3 | 126 | 73 |
| K.G. | Male | 46 | 105 | 60 | F | 8 | 128 | 75 | 3 | 125 | 72 |
| K.Y. | Female | 34 | 100 | 64 | A | 6 | 124 | 80 | 4 | 126 | 77 |
| N.M. | Female | 32 | 108 | 62 | E | 3 | 128 | 78 | 3 | 126 | 76 |

TABLE 13-continued

| | | | Blood Pressure before treatment (mmHg) | | Treatment | | Blood pressure after treatment (mmHg) | | After discontinuance of treatment | | |
|---|---|---|---|---|---|---|---|---|---|---|---|
| | | | | | | | | | Observation period (months) | Blood pressure (mmHg) | |
| Name | Patient Sex | Age | Maximum blood pressure | Minimum blood pressure | Type of capsule | Period (months) | Maximum blood pressure | Minimum blood pressure | | Maximum blood pressure | Minimum blood pressure |
| K.M. | Female | 29 | 104 | 56 | F | 3 | 126 | 74 | 3 | 127 | 73 |

EXAMPLE 1

| Tablet A | |
|---|---|
| Dried earthworm powder (having the same composition as previously described for M-3) | 150 mg |
| Manitol | 123 mg |
| Hydroxypropoxymethylcellulose | 7 mg |
| Talc | 5 mg |
| Microcrystalline cellulose | 60 mg |
| Hydrogenated castor oil | 5 mg |
| Total | 350 mg |

| Tablet B | |
|---|---|
| Dried earthworm powder (having the same composition as previously described for M-3) | 150 mg |
| Corn starch | 60 mg |
| Lactose | 80 mg |
| Talc | 7 mg |
| Magnesium stearate | 3 mg |
| Total | 300 mg |

| Tablet C | |
|---|---|
| Dried earthworm powder (having the same composition as previously described for M-3) | 150 mg |
| Soluble starch | 20 mg |
| Corn starch | 125 mg |
| Microcrystalline cellulose | 45 mg |
| Silicon oxide | 6 mg |
| Magnesium stearate | 4 mg |
| Total | 350 mg |

According to each of the above formulations, the ingredients were blended intimately. Then, using a tablet machine, the resulting powder blend was formed into tablets having the indicated weight.

EXAMPLE 2

| Granules A | |
|---|---|
| Dried earthworm powder (having the same composition as previously described for M-2) | 150 mg |
| Lactose | 20 mg |
| Microcrystalline cellulose | 60 mg |
| Corn starch | 15 mg |
| Hydroxypropylcellulose | 5 mg |
| Total | 250 mg |

According to the above formulation, granules were prepared by use of a fluidized bed granulating machine. Specifically, dried earthworm powder, lactose, microcrystalline cellulose and corn starch were blended well. The resulting powder blend was sprayed with a 5% aqueous solution of hydroxypropylcellulose as a binder and then dried at low temperature to form granules.

EXAMPLE 3

| Granules B | |
|---|---|
| Dried earthworm powder (having the same composition as previously described for M-2) | 100 mg |
| Mannitol | 10 mg |
| Microcrystalline cellulose | 85 mg |
| Carboxymethylcellulose calcium | 2 mg |
| Magnesium stearate | 1.5 mg |
| Hardened oil | 1.5 mg |
| Total | 200.0 mg |

| Granules C | |
|---|---|
| Dried earthworm powder (having the same composition as previously described for M-2) | 150 mg |
| Lactose | 53 mg |
| Corn starch | 39 mg |
| Potato starch | 2 mg |
| Talc | 3 mg |
| Magnesium stearate | 3 mg |
| Total | 250 mg |

According to each of the above formulations, the ingredients were blended well. Then, the resulting powder blend was granulated by use of an extruder.

EXAMPLE 4

| Capsule A | |
|---|---|
| Dried earthworm powder (having the same composition as previously described for M-2) | 150 mg |
| Lactose | 28 mg |
| Microcrystalline cellulose | 47 mg |
| Mannitol | 10 mg |
| Corn starch | 10 mg |
| Polyvinylpyrrolidone | 2 mg |
| Hydroxypropylcellulose | 3 mg |
| Total | 250 mg |

According to the above formulation, granules were prepared by use of a fluidized bed granulating machine. Specifically, all ingredients, except hydroxypropylcellulose, were blended well. The resulting powder blend was sprayed with a 5% aqueous solution of hydroxypropylcellulose as a binder and then dried at low temperature to form granules. Then, hard capsules were prepared by filling 250 mg each of the granules into hard shells.

EXAMPLE 5

Capsule B

Using granules C obtained in Example 3, hard capsules were prepared by filling 250 mg each of the granules into hard shells.

EXAMPLE 6

| Capsule C | |
| --- | --- |
| Dried earthworm powder (having the same composition as previously described for M-3) | 150 mg |
| Dibasic calcium phosphate | 60 mg |
| Dibasic sodium phosphate | 10 mg |
| Mannitol | 28 mg |
| Magnesium stearate | 2 mg |
| Total | 250 mg |

According to the above formulation, the ingredients were blended well. Then, capsules were prepared by filling 250 mg each of the resulting powder blend into No. 1 gelatin shells.

EXAMPLE 7

| Enteric tablet | |
| --- | --- |
| Dried earthworm powder (having the same composition as previously described for M-1) | 100 mg |
| Mannitol | 10 mg |
| Microcrystalline cellulose | 85 mg |
| Carboxymethylcellulose calcium | 2 mg |
| Magnesium stearate | 1.5 mg |
| Hardening agent | 1.5 mg |
| Total | 200 mg |

According to the above formulation, the ingredients were blended intimately and the resulting powder blend was formed into tablets by use of a tablet machine. Then, enteric tablets were formed by coating the above tablets with the following enteric coating composition.

| Coating composition | |
| --- | --- |
| Hydroxypropylmethylcellulose phthalate | 14.8 mg |
| Dioctyl phthalate | 2.3 mg |
| Stearic acid | 2.3 mg |
| Light silicon oxide | 0.6 mg |
| | 20.0 mg |

EXAMPLE 8

| Powder A | |
| --- | --- |
| Dried earthworm powder (having the same composition as previously described for M-4) | 150 mg |
| Mannitol | 50 mg |
| Corn starch | 50 mg |
| Total | 250 mg |

| Powder B | |
| --- | --- |
| Dried earthworm powder (having the same composition as previously described for M-4) | 150 mg |
| Dibasic calcium phosphate | 20 mg |
| Corn starch | 80 mg |
| Total | 250 mg |

According to each of the above formulations, powders were prepared by blending the ingredients intimately in a conical mixer.

EXAMPLE 9

| Suppository A | |
| --- | --- |
| Dried earthworm powder (having the same composition as previously described for M-5) | 200 mg |
| Witepsol E-85 | 540 mg |
| Witepsol W-35 | 1,454 mg |
| Methyl p-hydroxybenzoate | 3 mg |
| Butyl p-hydroxybenzoate | 3 mg |
| Total | 2,200 mg |

| Suppository B | |
| --- | --- |
| Dried earthworm powder (having the same composition as previously described for M-6) | 200 mg |
| Butyl hydroxyanisole | 6 mg |
| Semisynthetic glyceride | 2,900 mg |
| Total | 3,106 mg |

According to each of the above formulations, the ingredients were blended well and melted. Then, suppositories were formed by pouring the melt into aluminum molds and then cooling the molds.

EXAMPLE 10

| Capsule D | |
| --- | --- |
| Dried earthworm powder (having the same composition as previously described for M-2) | 150 mg |
| Sodium lauryl sulfate | 4 mg |
| Dibasic sodium phosphate | 1 mg |
| Mannitol | 93 mg |
| Magnesium stearate | 2 mg |
| Total | 250 mg |

According to the above formulation, the ingredients were blended well. Then, capsules were prepared by filling 250 mg each of the resulting powder blend into No. 1 gelatin shells.

EXAMPLE 11

| Capsule E | |
| --- | --- |
| Dried earthworm powder (having the same composition as previously described for M-4) | 150 mg |
| Dibasic calcium phosphate | 60 mg |
| Dibasic sodium phosphate | 10 mg |
| Mannitol | 28 mg |
| Magnesium stearate | 2 mg |
| Total | 250 mg |

According to the above formulation, the ingredients were blended well. Then, capsules were prepared by filling 250 mg each of the resulting powder blend into No. 1 gelatin shells.

EXAMPLE 12

| Capsule F | |
| --- | --- |
| Dried earthworm powder (having the same composition as previously described for M-5) | 150 mg |
| Sodium lauryl sulfate | 2 mg |
| Dibasic sodium phosphate | 4 mg |
| Mannitol | 92 mg |
| Magnesium stearate | 2 mg |

|Capsule F||
|---|---|
|Total|250 mg|

According to the above formulation, the ingredients were blended well. Then, capsules were prepared by filling 250 mg each of the resulting powder blend into No. 1 gelatin shells.

EXAMPLE 13

One kilogram of (about 20,000) living earthworms (*Lumbricus rubellus*) were gently washed with water and then placed in 4 liters of an acidic aqueous solution (pH 6.2) containing malic acid and citric acid in a ratio of 1:1. The living earthworms were left therein at a temperature of 8° C. for 3 hours, so that the aliminatary canal thereof was substantially freed of soil. Thereafter, the living earthworms were thoroughly washed with water to remove any dirt (such as mud and excreta) from the body surfaces thereof.

Subsequently, the living earthworms were wet-ground in a mixer. The resulting suspension was placed in a tray and frozen at −30° C. for 40 hours. Then, while the frozen suspension was maintained at −40° C., it was freeze-dried under a vacuum of 0.1 mmHg for 6 hours. After the temperature of the shelf having the tray placed thereon was raised to 30° C., the resulting powder was vacuum-dried under a vacuum of 0.1 mmHg for 6 hours. Thereafter, the powder was further vacuum-dried at a shelf temperature of 50° C. under a vacuum of 0.2 mmHg for 10 hours, and then at a shelf temperature of 80° C. under a vacuum of 0.2 mmHg for 8 hours. Thus, there was obtained 280 g of a dried earthworm powder product (M-1).

EXAMPLE 14

One kilogram of living earthworms (*Lumbricus rubellus*) were gently washed with water and then placed in 3 liters of an acidic aqieous solution (pH 5.5) containing phosphoric acid, tartaric acid and lactic acid in a ratio of 1:1:1. The living earthworms were left therein at a temperature of 10° C. for 2.5 hours, so that the aliminatary canal thereof was substantially freed of soil. Thereafter, the living earthworms were thoroughly washed with water to remove any dirt (such as mud and excreta) from the body surfaces thereof.

Subsequently, the living earthworms were wet-ground in a mixer. The resulting suspension was placed in a tray and frozen at −25° C. for 20 hours. Then, while the frozen suspension was maintained at −35° C., it was freeze-dried under a vacuum of 0.1 mmHg for 7 hours. After the temperature of the shelf having the tray placed thereon was raised to 28° C., the resulting powder was vacuum-dried under a vacuum of 0.1 mmHg for 10 hours. Thereafter, the powder was further vacuum-dried at a shelf temperature of 40° C. under a vacuum of 0.2 mmHg for 13 hours, and then at a shelf temperature of 78° C. under a vacuum of 0.1 mmHg for 8 hours. Thus, there was obtained 275 g of a dried earthworm powder product (M-2).

EXAMPLE 15

One kilogram of living earthworms (*Lumbricus rubellus*) were gently washed with water and then placed in 2 liters of an acidic aqueous solution (pH 5.8) containing malic acid. The living earthworms were left therein at a temperature of 13° C. for 3 hours, so that the aliminatary canal thereof was substantially freed of soil. Thereafter, the living earthworms were thoroughly washed with water to remove any dirt (such as mud and excreta) from the body surfaces thereof. Subsequently, the living earthworms were wet-ground in an ultrahomomixer (manufactured by Nippon Seiki K. K.). The resulting suspension was placed in a tray and frozen at −30° C. for 30 hours. Then, while the frozen suspension was maintained at −30° C., it was freeze-dried under a vacuum of 0.1 mmHg for 8 hours. After the temperature of the shelf having the tray placed thereon was raised to 25° C., the resulting powder was vacuum-dried under a vacuum of 0.1 mmHg for 7 hours. Thereafter, the powder was further vacuum-dried at a shelf temperature of 45° C. under a vacuum of 0.1 mmHg for 12 hours, and then at a shelf temperature of 80° C. under a vacuum of 0.1 mmHg for 7 hours. Thus, there was obtained 275 g of a dried earthworm powder product (M-4).

EXAMPLE 16

One kilogram of living earthworms (*Lumbricus rubellus*) were gently washed with water and then left in 3 liters of fresh water at a temperature of 10° C. for 16 hours, so that the aliminatary canal thereof was substantially freed of soil. Thereafter, the living earthworms were thoroughly washed with water to remove any dirt (such as mud and excreta) from the body surfaces thereof. Subsequently, the living earthworms were wet-ground in an ultrahomomixer. The resulting suspension was placed in a tray and frozen at −25° C. for 15 hours. Then, while the frozen suspension was maintained at −35° C., it was freeze-dried under a vacuum of 0.1 mmHg for 6 hours. After the temperature was raised to 30° C., the resulting powder was dried under a vacuum of 0.08 mmHg for 10 hours. Thereafter, the powder was further dried at a temperature of 40° C. under a vacuum of 0.2 mmHg for 15 hours, and then at a temperature of 78° C. under a vacuum of 0.1 mmHg for 8 hours. Thus, there was obtained 245 g of a dried earthworm powder product (M-3).

EXAMPLE 17

One kilogram of living earthworms (*Lumbricus rubellus*) were thoroughly washed five times with water to remove any dirt (such as mud and straw fragments) from the body surfaces thereof. Then, the living earthworms were left in 2.5 liters of fresh water at a temperature of 15° C. for 18 hours, so that the aliminatary canal thereof was substantially freed of soil. Subsequently, the living earthworms were gently washed with water and then wet-ground in an ultrahomomixer. The resulting suspension was placed in a tray and frozen at −40° C. for 24 hours. Then, while the frozen suspension was maintained at −40° C., it was freeze-dried under a vacuum of 0.1 mmHg for 5 hours. After the temperature was raised to 25° C., the resulting powder was dried under a vacuum of 0.1 mmHg for 8 hours. Thereafter, the powder was further dried at a temperature of 45° C. under a vacuum of 0.1 mmHg for 12 hours, and then at a temperature of 80° C. under a vacuum of 0.1 mmHg for 7 hours. Thus, there was obtained 240 g of a dried earthworm powder product (M-5).

EXAMPLE 18

One kilogram of living earthworms (*Lumbricus rubellus*) were thoroughly washed four times with water to remove any dirt (such as mud and excreta) from the body surfaces thereof. Then, the living earthworms were placed in 2.5 liters of an acidic aqueous solution (pH 5.7) containing malic acid and lactic acid in a ratio of 1:1, and left therein at a temperature of 15° C. for 2.5 hours, so that the aliminatary canal thereof was freed of soil. Subsequently, the living earthworms were gently washed with water and then wet-ground in a mixer. The resulting suspension was was placed in a tray and frozen at −35° C. for 24 hours. Then, while the frozen suspension was maintained at −35° C., it was freeze-dried under a vacuum of 0.1 mmHg for 7 hours. After the temperature of the shelf having the tray placed thereon was raised to 22° C., the resulting powder was vacuum-dried under a vacuum of 0.1 mmHg for 10 hours. Thereafter, the powder was further dried at a shelf temperature of 42° C. under a vacuum of 0.2 mmHg for 15 hours, and finally at a shelf temperature of 78° C. under a vacuum of 0.1 mmHg for 7 hours. Thus, there was obtained 265 g of a dried earthworm powder product (M-6).

EXAMPLE 19

1.5 g of monobasic potassium phosphate was dissolved in 2.5 liters of an acidic aqueous solution (pH 6.0) containing citric acid. One kilogram of living earthworms (Pheretima communissima) were gently washed with water, placed in the above solution, and left therein at a temperature of 10° C. for 2 hours, so that the aliminatary canal thereof was freed of soil. Thereafter, the living earthworms were washed twice with water to remove any dirt (such as mud, excreta and straw fragments) from the body surfaces thereof. Subsequently, the living earthworms were wet-ground in a mixer. The resulting suspension was freeze-dried and vacuum-dried in the same manner as described in Example 17. Thus, there was obtained 280 g of dried earthworm powder.

EXAMPLE 20

One kilogram of living earthworms (Allolobophora caliginosa) were thoroughly washed five times with water to remove any dirt (such as mud, excreta and straw fragments) from the body surfaces thereof. Then, the living earthworms were placed in 3 liters of an acidic aqueous solution (pH 5.7) containing succinic acid (and additionally containing 1 g of sodium acetate and 0.5 g of sodium sulfate), and left therein at a temperature of 13° C. for 2.5 hours, so that the aliminatary canal thereof was freed of soil.

Subsequently, the living earthworms were gently washed with water and then wet-ground in a homogenizer. The resulting suspension was freeze-dried and vacuum-dried in the same manner as described in Example 18. Thus, there was obtained 275 g of dried earthworm powder.

EXAMPLE 21

One kilogram of living earthworms (Pheretima communissima) were thoroughly washed five times with water to remove any dirt (such as mud, excreta and straw fragments) from the body surfaces thereof. Then, the living earthworms were placed in 2.5 liters of an acidic aqueous solution (pH 5.9) containing citric acid and tartaric acid in a ratio of 1:1 (and additionally containing 0.7 g of potassium citrate), and left therein at a temperature of 15° C. for 2 hours, so that the aliminatary canal thereof was freed of soil. Subsequently, the living earthworms were gently washed with water and then wet-ground in a blender. The resulting suspension was freeze-dried and vacuum-dried in the same manner as described in Example 18. Thus, there was obtained 283 g of dried earthworm powder.

As described above, the present invention relates to a process for the production of dried earthworm powder which comprises the steps of leaving a species of living earthworms in fresh water or a slightly acidic aqueous solution until the alimentary canal thereof is freed of soil, wet-grinding the living earthworms, and freeze-drying or vacuum-drying the resulting suspension under a vacuum of 10 mmHg or below for 10 to 100 hours while raising the temperature stepwise from −60° C. to 80° C., and to antihyperlipemic, antidiabetic, antihypertensive and antihypotensive preparations containing the dried earthworm powder as the active ingredient.

The enzymes present in the dried earthworm powder produced by the novel and improved process of the present invention are not destroyed or inactivated. Moreover, the sterile dried earthworm powder produced by the process of the present invention can be preserved or stored in a well-closed state for at least 4 years. Furthermore, the dried earthworm powder can be obtained in a high yield of 20 to 35% based on the living earthworm used as the raw material.

By experiments in which rats were fed, for 1 week or 4 weeks, with a high-cholesterol diet containing the dried earthworm powder produced by the process of the present invention, it has been found that the dried earthworm powder of the present invention has an excellent antihyperlipemic effect. In the 1-week experiment, the dried earthworm powder containing diet groups showed a statistically significant reduction in serum TC, FC, LDL-C and AI, as comprated with the high-cholesterol diet group. However, no significant change in serum HDL-C was observed. In the 4-week experiment, the dried earthworm powder containing diet groups showed a significant reduction in serum TC, FC, PL and NEFA, as compared with the high-cholesterol diet group. Moreover, it was demonstrated that HDL-C (considered to be an arteriosclerosis improving factor) was elevated significantly and AI was reduced significantly. TG was not reduced significantly, although a tendency of reduction was indicated. GOT and GPT were reduced significantly.

The weight of the liver and the levels of TC and PL in liver lipids were reduced significantly, but TG showed no essential change. The body weight of the rats increased steadily without showing any significant variation.

Then, dried earthworm powder capsules (each containing 150 mg) were orally administered to 4 volunteers for 6 or 7 months. The dosage was such that one capsule was given three times a day after each meal. During the treatment, the serum TC, TG, HDL-C and AI levels were determined. As a result, TC and AI were markedly reduced after 3 or 4 months and thencefoward. On the other hand, HDL-C made no appreciable change, but showed a slight rising tendency after 6 or 7 months. TG showed a distinct reduction after 6 or 7 months.

The above-described animal experiments and the experiment concerning oral administration to human subjects have revealed that the dried earthworm powder of the present invention is a safe and excellent drug which is useful for the treatment and prevention of hyperlipemia, for the improvement of serum lipid metabolism, and for the treatment and prevention of arteriosclerosis.

The present invention also relates to antidiabetic preparations containing dried earthworm powder as the active ingredient. When the dried earthworm powder was administered to mice with diabetes experimentally induced by alloxan, the blood sugar level was reduced to a statistically significant degree.

Then, dried earthworm powder capsules (each containing 150 mg), in combination with alimentotherapy, was orally administered to 5 volunteers who were diabetic patients. The dosage was such that one capsule was given three times a day after each meal, and the treatment was continued for 4 to 9 months. After 1, 2, 3 or 4 months of treatment, blood sugar determinations were made at intervals of at least 1 month. For this purpose, six blood samples were collected before breakfast, two hours after breakfast, before lunch, two hours after lunch, before supper, and two hours after supper, and analyzed for blood sugar level. As a result, the patients with a mild or moderate degree of diabetes began to show an improvement after 2 or 3 months of treatment with the dried earthworm powder. Eventually, all of the six test values could be restored to their normal levels (50-100 mg/dl for the test value obtained two hours after each meal) after 4 months of treatment and thenceforward. In the patient with a severe degree of diabetes, it was somewhat difficult to restore all of the six test values to their normal levels. After 8 months of treatment, however, an improvement was achieved in that four of the six test values were restored to their normal levels. Even prolonged administration over a period of 6 to 9 months involved no risk of causing hypoglycemia in which blood sugar would be reduced to a level below the lower limit of its normal range. Thus, the dried earthworm powder of the present invention has been found a safe and excellent drug useful for the treatment and prevention of diabetes.

The present invention further relates to blood pressure regulator preparations, or antihypertensive and/or hypotensive preparations, containing dried earthworm powder as the active ingredient. When the dried earthworm powder of the present invention was orally administered to SHRs, a blood pressure reduction of 28 to 35 mmHg was observed 1 to 2 hours after administration and this hypotensive effect lasted 6 hours. The dried earthworm powder of the present invention did not produce side effects such as tachycardia and hemolysis, and was found to be a safe drug having good preservability (or storability).

Moreover, dried earthworm powder capsules (each containing 150 mg) prepared in accordance with the present invention were orally administered to 14 volunteers (8 hypertensive patients and 6 hypotensive patients) for 2 to 11 months. The dosage was such that one capsule was given three times a day after each meal. These preparations had the effect of reducing the blood pressure of hypertensive patients and elevating the blood pressure of hypotensive patients, thereby restoring the blood pressure of these patients to its normal levels. Moreover, the normal blood levels achieved by these preparations were maintained for 3 to 7 months. During the period of the treatment, neither abnormal reduction nor abnormal elevation in blood pressure occurred, and other side effects were not observed at all.

Thus, the preparations of the present invention have been found to be safe and excellent medicines useful as blood pressure modulators (or remedies for hypertension and/or hypotension) or preventives for hypertension and/or hypotension.

What is claimed is:

1. A process for the production of dried earthworm powder which comprises the steps of
   (a) cleaning a species of living earthworms by leaving the living earthworms in an aqueous solution containing not greater than 0.3% by weight of at least one compound selected from the group consisting of an organic acid, an inorganic acid, a sodium salt of an organic acid, a sodium salt of an inorganic acid, a potassium salt of an organic acid, and a potassium salt of an inorganic acid, until the alimentary canal thereof is freed of soil, and then washing the living earthworms with water to remove any dirt from the body surfaces thereof, or by washing the living earthworms with water to remove any dirt from the body surface thereof, and then leaving the living earthworms in said aqueous solution until the alimentary canal thereof is freed of soil;
   (b) wet-grinding the living earthworms;
   (c) freezing the resulting suspension at a temperature of $-60°$ to $-10°$ C.; and
   (d) freeze-drying and then vacuum-drying the suspension under a vacuum of 10 mmHg or below for 10 to 100 hours while raising the temperature stepwise in the range of $-60°$ to 80° C., the resulting powder being finally vacuum-dried at a temperature of 70° to 80° C. under a vacuum of 0.01 to 0.5 mmHg for 5 to 10 hours.

2. A process for the production of dried earthworm powder which comprises the steps of
   (a) cleaning a species of living earthworms by leaving the living earthworms in fresh water at a temperature of 8° to 22° C. for 14 to 20 hours until the alimentary canal thereof is freed of soil, and then washing the living earthworms with water to remove any dirt from the body surfaces thereof, or by washing the living earthworms with water to remove any dirt from the body surfaces thereof, and then leaving the living earthworms in said fresh water until the alimentary canal thereof is freed of soil;
   (b) wet-grinding the living earthworms;
   (c) freezing the resulting suspension at a temperature of $-60°$ to $-10°$ C.; and
   (d) freeze-drying and then vacuum-drying the suspension under a vacuum of 10 mmHg or below for 10 to 100 hours while raising the temperature stepwise in the range of $-60°$ to 80° C., the resulting powder being finally vacuum-dried at a temperature of 70° to 80° C. under a vacuum of 0.01 to 0.5 mmHg for 5 to 10 hours.

3. A process as claimed in claim 1 wherein the organic acid is acetic acid, citric acid, succinic acid, malic acid, tartaric acid or lactic acid.

4. A process as claimed in claim 1 wherein the inorganic acid is phosphoric acid, sulfuric acid or hydrochloric acid.

* * * * *